United States Patent [19]
Dietrich

[11] Patent Number: 5,767,361
[45] Date of Patent: Jun. 16, 1998

[54] IMIDAZOLINONE RESISTANT AHAS MUTANTS

[75] Inventor: Gabriele Elfriede Dietrich, Rocky Hill, N.J.

[73] Assignee: American Cyanamid Company, Me.

[21] Appl. No.: 894,062

[22] Filed: Jun. 8, 1992

Related U.S. Application Data

[63] Continuation-in-part of Ser. No. 737,851, Jul. 31, 1991.

[51] Int. Cl.$^6$ .............................. A01H 5/00; A01H 5/10; C12N 15/00; A01G 1/00
[52] U.S. Cl. ................... 800/205; 800/250; 800/255; 800/200; 435/172.3; 47/58
[58] Field of Search ........................... 800/205, 200, 800/250, 255; 435/172.3; 47/58

[56] References Cited

U.S. PATENT DOCUMENTS 4,761,373   8/1988   Anderson et al. ................... 435/172.3

OTHER PUBLICATIONS

G.W. Haughn et al. Mol. Gen. Genet., vol. 211 (1988) pp. 266–271.
P.A. Wiersma et al. Mol. Gen. Genet., vol. 219 (1989) pp. 413–420.
G.C. Jen et al. J. Cellular Biochem. Suppl. 14E (1990) p. 302.
R.W. Old et al., Principles of Genetic Manipulation 4th Ed, Oxford, UK. Blackwell Scientific Publ., 1989, pp. 87–98.
Sathasivan, K., et al Nucleic Acids Research, vol. 18 (1990) p. 2188.
Haughn, G., et al. Plant Physiology, vol. 92 (1990) pp. 1081–1085.

*Primary Examiner*—Charles C. P. Rories
*Attorney, Agent, or Firm*—Darryl L. Webster; J. J. Harrington; K. A. Lowney

[57] ABSTRACT

The present invention relates to monocot genes encoding a mutant AHAS enzyme that is specifically resistant to imidazolinone herbicides. Exemplary of these genes are corn DNA sequences which encode an amino acid substitution at position 621 of the wild-type AHAS enzyme. The mutant gene can be used to transform other plants to herbicide resistance; in this regard, the invention also provides host cells and vectors containing the gene, which cells and vectors are useful in the transformation process.

41 Claims, 29 Drawing Sheets

▼ SalI
□ XhoI
◇ HindIII
○ XbaI
● ClaI
■ PstI

W22/1A and B73/7-4 sequence:  5'TAGTG3'
3'ATCTG5'

XII2/8A sequence: 5'TAATG3'
3'ATTAC5'

FIG. 6A

```
         40               50              60              70              80              90
          *                *               *               *               *               *
        ATG GCC ACC GCC GCC GCC GCG TCT ACC GCG CTC ACT GGC GCC ACT ACC GCT GCG
        Met Ala Thr Ala Ala Ala Ala Ser Thr Ala Leu Thr Gly Ala Thr Thr Ala Ala 100             110             120             130             140
                        *               *               *               *               *
        CCC AAG GCG AGG CGC AGG CGG GCG CAC CTC CTG GCC ACC CGC GCC CTC GCC GCG
        Pro Lys Ala Arg Arg Arg Arg Ala His Leu Leu Ala Thr Arg Ala Leu Ala Ala 150             160             170             180             190
                        *               *               *               *               *
        CCC ATC AGG TGC TCA GCG GCG TCA CCC GCC ATG CCG ATG GCT CCC CCG GCC ACC
        Pro Ile Arg Cys Ser Ala Ala Ser Pro Ala Met Pro Met Ala Pro Pro Ala Thr 200             210             220             230             240             250
         *               *               *               *               *               *
        CCG CTC CGG CCG TGG GGC CCC ACC GAT CCC CGC AAG GGC GCC GAC ATC CTC GTC
        Pro Leu Arg Pro Trp Gly Pro Thr Asp Pro Arg Lys Gly Ala Asp Ile Leu Val 260             270             280             290             300
         *               *               *               *               *
        GAG TCC CTC GAG CGC TGC GGC GTC CGC GAC GTC TTC TGC TAC CCC GGC GGC GCG
        Glu Ser Leu Glu Arg Cys Gly Val Arg Asp Val Phe Cys Tyr Pro Gly Gly Ala
```

FIG. 6B

```
310             320             330             340             350             360
 *               *               *               *               *               *
TCC ATG GAG ATC CAC CAG GCA CTC ACC CGC TCC CCC GTC ATC GCC AAC CAC CTC
Ser Met Glu Ile His Gln Ala Leu Thr Arg Ser Pro Val Ile Ala Asn His Leu 370             380             390             400             410
      *               *               *               *               *
TTC CGC CAC GAG CAA GGG GAG GCC TTT GCG GCC TCC TAC GGC TCC CGC TCC TCG
Phe Arg His Glu Gln Gly Glu Ala Phe Ala Ala Ser Gly Tyr Ala Arg Ser Ser 420             430             440             450             460
 *               *               *               *               *
GGC CGC GTC GGC GTC TGC ATC GCC ACC TCC GGC GCC ACC AAC CTT GTC
Gly Arg Val Gly Val Cys Ile Ala Thr Ser Gly Pro Gly Ala Thr Asn Leu Val 470             480             490             500             510             520
 *               *               *               *               *               *
TCC GCG CTC GCC GAC GCG CTG CTC GAT TCC GTC CCC ATG GTC GCC ATC ACG GGA
Ser Ala Leu Ala Asp Ala Leu Leu Asp Ser Val Pro Met Val Ala Ile Thr Gly
```

FIG. 6C

```
    530         540         550         560         570         630
     *           *           *           *           *           *
CAG GTG CCG CGA CGC ATG ATT GGC ACC GAC GCC TTC CAG GAG ACG CCC ATC GTC
Gln Val Pro Arg Arg Met Ile Gly Thr Asp Ala Phe Gln Glu Thr Pro Ile Val 580         590         600         610         620         630
     *           *           *           *           *           *
GAG GTC ACC CGC TCC ATC ACC AAG CAC AAC TAC CTG GTC GAC CTC GAC GAC
Glu Val Thr Arg Ser Ile Thr Lys His Asn Tyr Leu Val Leu Asp Val Asp Asp 640         650         660         670         680
     *           *           *           *           *
ATC CCC CGC GTC GTG CAG GAG GCT TTC CTC GCC TCC TCT GGT CGA CCG GGG
Ile Pro Arg Val Val Gln Glu Ala Phe Leu Ala Ser Ser Gly Arg Pro Gly 690         700         710         720         730
     *           *           *           *           *
CCG GTG CTT GTC GAC ATC CCC AAG GAC ATC CAG CAG ATG GCG GTG CCT GTC
Pro Val Leu Val Asp Ile Pro Lys Asp Ile Gln Gln Met Ala Val Pro Val
```

FIG. 6D

```
740
 *
TGG GAC AAG CCC ATG AGT CTG CCT GGG TAC ATT GCG CGC CTT CCC AAG CCC CCT
Trp Asp Lys Pro Met Ser Leu Pro Gly Tyr Ile Ala Arg Leu Pro Lys Pro Pro
        750          760          770          780          790
         *            *            *            *            *

GCG ACT GAG TTG CTT GAG CAG GTG CTG CGT CTT GTT GGT GAA TCC CGG CGC CCT
Ala Thr Glu Leu Leu Glu Gln Val Leu Arg Leu Val Gly Glu Ser Arg Arg Pro
        800          810          820          830          840
         *            *            *            *            *

GTT CTT TAT GTT GGC GGT GCG TGC GCA GCA TCT GGT GAG GAG TTG CGA CGC TTT
Val Leu Tyr Val Gly Gly Ala Cys Ala Ala Ser Gly Glu Glu Leu Arg Arg Phe
        850          860          870          880          890          900
         *            *            *            *            *            *

GTG GAG CTG ACT GGA ATC CCG GTC ACA ACT CTT ATG GGC CTC GGC AAC TTC
Val Glu Leu Thr Gly Ile Pro Val Thr Thr Leu Met Gly Leu Gly Asn Phe
        910          920          930          940          950
         *            *            *            *            *
```

FIG. 6E

```
       960            970            980            990            1000
        *              *              *              *              *
CCC AGC GAC GAC CCA CTG TCT CTG CGC ATG CTA GGT ATG CAT GGC ACG GTG TAT
Pro Ser Asp Asp Pro Leu Ser Leu Arg Met Leu Gly Met His Gly Thr Val Tyr 1010           1020            1030            1040            1050            1060
    *              *              *              *              *              *
GCA AAT TAT GCA GTG GAT AAG GCC GAT CTG TTG CTT GGT GTG CGG TTT
Ala Asn Tyr Ala Val Asp Lys Ala Asp Leu Leu Leu Ala Leu Gly Val Arg Phe 1070            1080            1090            1100            1110
            *              *              *              *              *
GAT GAT CGT GTG ACA GGG AAG ATT GAG GCT TTT GCA AGC AGG GCT AAG ATT GTG
Asp Asp Arg Val Thr Gly Lys Ile Glu Ala Phe Ala Ser Arg Ala Lys Ile Val 1120           1130            1140            1150            1160            1170
    *              *              *              *              *              *
CAC GTT GAT ATT GAT CCG GCT GAG ATT GGC AAG AAC AAG CAG CCA CAT GTG TCC
His Val Asp Ile Asp Pro Ala Glu Ile Gly Lys Asn Lys Gln Pro His Val Ser
```

FIG. 6F

```
              1180            1190            1200            1210            1220
                *               *               *               *               *
ATC TGT GCA GAT GTT AAG CTT GCT TTG CAG GGC ATG AAT GCT CTT GAA GGA
Ile Cys Ala Asp Val Lys Leu Ala Leu Gln Gly Met Asn Ala Leu Glu Gly 1230            1240            1250            1260            1270
        *               *               *               *               *
AGC ACA TCA AAG AAG AGC TTT GAC TTT GGC TCA TGG AAC GAT GAG TTG GAT CAG
Ser Thr Ser Lys Lys Ser Phe Asp Phe Gly Ser Trp Asn Asp Glu Leu Asp Gln 1280            1290            1300            1310            1320            1330
  *               *               *               *               *               *
CAG AAG AGG GAA TTC CCC CTT GGG TAT AAA ACA TCT AAT GAG GAG ATC CAG CCA
Gln Lys Arg Glu Phe Pro Leu Gly Tyr Lys Thr Ser Asn Glu Glu Ile Gln Pro 1340            1350            1360            1370            1380
        *               *               *               *               *
CAA TAT GCT ATT CAG GTT CTT GAT GAG CTG ACG AAA GGC GAG ATC ATC GGC
Gln Tyr Ala Ile Gln Val Leu Asp Glu Leu Thr Lys Gly Glu Ala Ile Gly
```

FIG. 6G

```
      1390            1400            1410            1420            1430            1440
       *               *               *               *               *               *
ACA GGT GTT GGG CAG CAC CAG ATG TGG GCG GCA CAG TAC ACT TAC AAG CGG
Thr Gly Val Gly Gln His Gln Met Trp Ala Ala Gln Tyr Thr Tyr Lys Arg 1450            1460            1470            1480            1490
       *               *               *               *               *
CCA AGG CAG TGG TTG TCT TCA GCT GGT CTT GGG GCT ATG GGA TTT GGT TTG CCG
Pro Arg Gln Trp Leu Ser Ser Ala Gly Leu Gly Ala Met Gly Phe Gly Leu Pro 1500            1510            1520            1530            1540
       *               *               *               *               *
GCT GCT GCT GGT GCT TCT GTG GCC AAC CCA GGT ACT GTT GAC ATC GAT
Ala Ala Ala Gly Ala Ser Val Ala Asn Pro Gly Val Thr Val Asp Ile Asp 1550            1560            1570            1580            1590            1600
       *               *               *               *               *               *
GGA GAT GGT AGC TTT CTC ATG AAC GTT CAG GAG CTA GCT ATG ATC CGA ATT GAG
Gly Asp Gly Ser Phe Leu Met Asn Val Gln Glu Leu Ala Met Ile Arg Ile Glu
```

FIG. 6H

```
         1610           1620           1630           1640           1650
          *              *              *              *              *
AAC CTC CCG GTG AAG GTC TTT GTG CTA AAC AAC CAG CAC CTG GGG ATG GTG GTG
Asn Leu Pro Val Lys Val Phe Val Leu Asn Asn Gln His Leu Gly Met Val Val 1660           1670           1680           1690           1700           1710
          *              *              *              *              *              *
CAG TGG GAG GAC AGG TTC TAT AAG GCC AAC AGA GCG CAC ACA TAC TTG GGA AAC
Gln Trp Glu Asp Arg Phe Tyr Lys Ala Asn Arg Ala His Thr Tyr Leu Gly Asn 1720           1730           1740           1750           1760
          *              *              *              *              *
CCA GAG AAT GAA AGT GAG ATA TAT CCA GAT TTC GTG ACG ATC GCC AAA GGG TTC
Pro Glu Asn Glu Ser Glu Ile Tyr Pro Asp Phe Val Thr Ile Ala Lys Gly Phe 1770           1780           1790           1800           1810
          *              *              *              *              *
AAC ATT CCA GCG GTC CGT GTG ACA AAG AAC GAA GTC CGC GCA ATA AAG
Asn Ile Pro Ala Val Arg Val Thr Lys Asn Glu Val Arg Ala Ile Lys
```

FIG. 6I

```
      1820        1830        1840        1850        1860        1870
        *           *           *           *           *           *
      AAG ATG CTC GAG ACT CCA GGG CCG TAC CTC TTG GAT ATA ATC GTC CCA CAC CAG
      Lys Met Leu Glu Thr Pro Gly Pro Tyr Leu Leu Asp Ile Ile Val Pro His Gln 1880        1890        1900        1910        1920
        *           *           *           *           *
      GAG CAT GTG TTG CCT ATG ATC CCT AAT GGT GGG GCT TTC AAG GAT ATG ATC CTG
      Glu His Val Leu Pro Met Ile Pro Asn Gly Gly Ala Phe Lys Asp Met Ile Leu 1930        1940        1950        1960
        *           *           *           *
      GAT GGT GAT GGC AGG ACT GTG TAC TGATC TAAAAA TCCAG CAAG
      Asp Gly Asp Gly Arg Thr Val Tyr
```

FIG. 7A

```
                       10          20          30          40          50
                AACCC TCGCG CCGCC TCCGA GACAG CCGCC GCAAC CATGG CCACC GCCGC CGCCG CGTCT
         B73/7-4 11111 11111 11111 11111 11111 11111 11111 11111 11111 11111 11111 11111
         W22/1A  AACCC TCGCG CCGCC TCCGA GACAG CCGCC GCAAC CATGG CCACC GCCGC CGCCG CGTCT
                 11111 11111 11111 11111 11111 11111 11111 11111 11111 11111 11111 11111
         XI12/8A AACCC TCGCG CCGCC TCCGA GACAG CCGCC GCAAC CATGG CCACC GCCGC CGCCG CGTCT
                 11111 11111 11111 11111 11111 11111 11111 11111 11111 11111 11111 11111

70          80          90         100         110         120
         XI12/8A ACCGC GCTCA CTGGC GCCAC TACCG CTGCG CCCAA GGCGC GCACC CGCCG TCCTG
         W22/1A  ACCGC GCTCA CTGGC GCCAC TACCG CTGCG CCCAA GGCGA GGCGC GCACC CGCCG TCCTG
                 11111 11111 11111 11111 11111 11111 11111 11111 11111 11111 11111 11111
         B73/7-4 ACCGC GCTCA CTGGC GCCAC TACCG CTGCG CCCAA GGCGA GGCGC GCACC CGCCG TCCTG
                 11111 11111 11111 11111 11111 11111 11111 11111 11111 11111 11111 11111
         XI12/8A ACCGC GCTCA CTGGC         TACCG CTGCG CCCAA GGCGA GGCGC GCACC CGCCG TCCTG 130         140         150         160         170         180
         XI12/8A GCCAC CCGCC GCGCC CTCGC CGGCG CCATC AGGTG CTCAG CGGCG TCACC CGCCA TGCCG
         W22/1A  GCCAC CCGCC GCGCC CTCGC CGGCG CCATC AGGTG CTCAG CGGCG TCACC CGCCA TGCCG
                 11111 11111 11111 11111 11111 11111 11111 11111 11111 11111 11111 11111
         B73/7-4 GCCAC CCGCC GCGCC CTCGC CGGCG CCATC AGGTG CTCAG CGGCG TCACC CGCCA TGCCG
                 11111 11111 11111 11111 11111 11111 11111 11111 11111 11111 11111 11111
```

FIG. 7B

```
                 190   200   210   220   230   240
XI12/8A          ATGGC TCCCC CGGCC ACCCC GCTCC GGCCG TGGGG CCCCA CCGAT CCCCG CAAGG GCGCC
W22/1A           ATGGC TCCCC CGGCC ACCCC GCTCC GGCCG TGGGG CCCCA CCGAT CCCCG CAAGG GCGCC
                 11111 11111 11111 11111 11111 11111 11111 11111 11111 11111 11111 11111
B73/7-4          ATGGC TCCCC CGGCC                                           GtGCt
                 11111 11111 11111                                           11111
XI12/8A          ATGGC TCCCC CGGCC ACCCC GCTCC GGCCG TGGGG CCCCA CCGAT CCCCG CAAGG GCGCC
                 11111 11111 11111 11111 11111 11111 11111 11111 11111 11111 11111 11111

250   260   270   280   290   300
XI12/8A          GACAT CCTCG TCGAG TCCCT CGAGC GCTGC GGCGT CCGCG ACGTC TTCGC CTACC CCGGC
W22/1A           GACAT CCTCG TCGAG TCCCT CGAGC GCTGC GGCGT CCGCG ACGTC TTCGC CTACC CCGGC
                 11111 11111 11111 11111 11111 11111 11111 11111 11111 11111 11111 11111
B73/7-4          GACAT CCTCG TCGAG TCCCT CGAGC GCTGC GGCGT CCGCG ACGTC TTCGC CTACC CCGGC
                 11111 11111 11111 11111 11111 11111 11111 11111 11111 11111 11111 11111
XI12/8A          GACAT CCTCG TCGAG TCCCT CGAGC GCTGC GGCGT CCGCG ACGTC TTCGC CTACC CCGGC
                 11111 11111 11111 11111 11111 11111 11111 11111 11111 11111 11111 11111

310   320   330   340   350   360
W22/1A           GGCGC GTCCA TGGAG ATCCA CCAGG CACTC ACCCG CTCCC CCGTC ATCGC CAACC ACCTC
                 11111 11111 11111 11111 11111 11111 11111 11111 11111 11111 11111 11111
XB73/7-4         GGCGC GTCCA TGGAG ATCCA CCAGG CACTC ACCCG CTCCC CCGTC ATCGC CAACC ACCTC
                 11111 11111 11111 11111 11111 11111 11111 11111 11111 11111 11111 11111
XI12/8A          GGCGC GTCCA TGGAG ATCCA CCAGG CACTC ACCCG CTCCC CCGTC ATCGC CAACC ACCTC
                 11111 11111 11111 11111 11111 11111 11111 11111 11111 11111 11111 11111
```

FIG. 7C

```
                370         380         390         400         410         420
XI12/8A    TTCCG CCACG AGCAA GGGGA GGCCT TTGCG GCCTC CGGCT ACGCG CGCTC CTCGG GCCGC

W22/1A     TTCCG CCACG AGCAA GGGGA GGCCT TTGCG GCCTC CGGCT ACGCG CGCTC CTCGG GCCGC
           11111 11111 11111 11111 11111 11111 11111 11111 11111 11111 11111 11111
B73/7-4    TTCCG CCACG AGCAA GGGGA GGCCT             GCCTC CGGCT ACGCG CGCTC CTCGG GCCGC
           11111 11111 11111 11111 11111             11111 11111 11111 11111 11111 11111
XI12/8A    TTCCG CCACG AGCAA GGGGA GGCCT TTGCG GCCTC CGGCT ACGCG CGCTC CTCGG GCCGC 430         440         450         460         470         480
XI12/8A    GTCGG CGTCT GCATC GCCAC CTCCG GCCCC CACCA ACCTT GTCTC               TCGCC

W22/1A     GTCGG CGTCT GCATC GCCAC CTCCG GCCCC CACCA ACCTT GTCTC CGGCG TCGCC
           11111 11111 11111 11111 11111 11111 11111 11111 11111 11111 11111 11111
B73/7-4    GTCGG CGTCT GCATC GCCAC CTCCG GCCCC CACCa ACCTT GTCTC CGGCG TCGCC
           11111 11111 11111 11111 11111 11111 11111 11111 11111 11111 11111 11111
XI12/8A    GTCGG CGTCT GCATC GCCAC CTCCG GCCCC CACCA ACCTT GTCTC               TCGCC 490         500         510         520         530         540
XI12/8A    GACGC GCTGC TCGAT TCCGT CCCCA TGGTC CACGG GACAG GTGCC GCGAC GCATG

W22/1A     GACGC GCTGC TCGAT TCCGT CCCCA TGGTC CACGG GACAG GTGCC GCGAC GCATG
           11111 11111 11111 11111 11111 11111 11111 11111 11111 11111 11111 11111
B73/7-4    GACGC GCTGC TCGAT TCCGT CCCCA TGGTC CACGG GACAG GTGCC GCGAC GCATG
           11111 11111 11111 11111 11111 11111 11111 11111 11111 11111 11111 11111
XI12/8A    GACGC GCTGC TCGAT TCCGT CCCCA TGGTC CACGG GACAG GTGCC GCGAC GCATG
```

FIG. 7D

|        | 550   |       |       | 560   |       |       | 570   |       |       | 580   |       |       | 590   |       |       | 600   |
|--------|-------|-------|-------|-------|-------|-------|-------|-------|-------|-------|-------|-------|-------|-------|-------|-------|
| XI12/8A | ATTGG | CACCG | ACGCC | TTCCA | GGAGA | CGCCC | ATCGT | CGAGG | TCACC | CGCTC | CATCA | CCAAG |
| W22/1A  | ATTGG | CACCG | ACGCC | TTCCA | GGAGA | CGCCC | ATCGT | CGAGG | TCACC | CGCTC | CATCA | CCAAG |
|         | 11111 | 11111 | 11111 | 11111 | 11111 | 11111 | 11111 | 11111 | 11111 | 11111 | 11111 | 11111 |
| B73/7-4 | ATTGG | CACCG | ACGCC | TTCCA | GGAGA | CGCCC | ATCGT | CGAGG | TCACC | CGCTC | CATCA | CCAAG |
|         | 11111 | 11111 | 11111 | 11111 | 11111 | 11111 | 11111 | 11111 | 11111 | 11111 | 11111 | 11111 |
| XI12/8A | ATTGG | CACCG | ACGCC | TTCCA | GGAGA | CGCCC | ATCGT | CGAGG | TCACC | CGCTC | CATCA | CCAAG |

|        | 610   |       |       | 620   |       |       | 630   |       |       | 640   |       |       | 650   |       |       | 660   |
|--------|-------|-------|-------|-------|-------|-------|-------|-------|-------|-------|-------|-------|-------|-------|-------|-------|
| XI12/8A | CACAA | CTACC | TGGTC | CTCGA | CGTCG | ACGAC | ATCCC | CCGCG | TCGTG | CAGGA | GGCTT | TCTTC |
| W22/1A  | CACAA | CTACC | TGGTC | CTCGA | CGTCG | ACGAC | ATCCC | CCGCG | TCGTG | CAGGA | GGCTT | TCTTC |
|         | 11111 | 11111 | 11111 | 11111 | 11111 | 11111 | 11111 | 11111 | 11111 | 11111 | 11111 | 11111 |
| B73/7-4 |       | CTACC | TGGTC | CTCGA | CGTCG | ACGAC | ATCCC | CCGCG | TCGTG | CAGGA | GGCTT | TCTTC |
|         | 11111 | 11111 | 11111 | 11111 | 11111 | 11111 | 11111 | 11111 | 11111 | 11111 | 11111 | 11111 |
| XI12/8A | CACAA | CTACC | TGGTC | CTCGA | CGTCG | ACGAC | ATCCC | CCGCG | TCGTG | CAGGA | GGCTT | TCTTC |

|        | 670   |       |       | 680   |       |       | 690   |       |       | 700   |       |       | 710   |       |       | 720   |
|--------|-------|-------|-------|-------|-------|-------|-------|-------|-------|-------|-------|-------|-------|-------|-------|-------|
| XI12/8A | CTCGC | CTCCT | CTGGT | CGACC | GGGGC | CGGTG | CTTGT | CGACA | TCCCC | AAGGA | CATCC | AGCAG |
| W22/1A  | CTCGC | CTCCT | CTGGT | CGACC | GGGGC | CGGTG | CTTGT | CGACA | TCCCC | AAGGA | CATCC | AGCAG |
|         | 11111 | 11111 | 11111 | 11111 | 11111 | 11111 | 11111 | 11111 | 11111 | 11111 | 11111 | 11111 |
| B73/7-4 | CTCGC | CTCCT | CTGGT | CGACC |       | CGGTG | CTTGT | CGACA | TCCCC | AAGGA | CATCC | AGCAG |
|         | 11111 | 11111 | 11111 | 11111 | 11111 | 11111 | 11111 | 11111 | 11111 | 11111 | 11111 | 11111 |
| XI12/8A | CTCGC | CTCCT | CTGGT | CGACC | GGGGC | CGGTG | CTTGT | CGACA | TCCCC | AAGGA | CATCC | AGCAG |

FIG. 7E

```
              730                740                750                 760               770              780
XI12/8A  CAGAT GGCGG TGCCT GTCTG GGACA AGCCC ATGAG TCTGC CTGGG TACAT TGCGC GCCTT

W22/1A   CAGAT GGCGG TGCCT GTCTG GGACA AGCCC ATGAG TCTGC CTGGG TACAT TGCGC GCCTT
         11111 11111 11111 11111 11111 11111 11111 11111 11111 11111 11111 11111
B73/7-4  CAGAT GGCGG TGCCT GTCTG GGACA AGCCC ATGAG TCTGC CTGGG TACAT TGCGC GCCTT
         11111 11111 11111 11111 11111 11111 11111 11111 11111 11111 11111 11111
XI12/8A  CAGAT GGCGG TGCCT GTCTG GGACA AGCCC ATGAG TCTGC CTGGG TACAT TGCGC GCCTT 790                800                810                 820               830              840
XI12/8A  CCCAA GCCCC CTGCG ACTGA GTTGC TTGAG CAGGT GCTGC                 GTTGG TGAAT CCCGG

W22/1A   CCCAA GCCCC CTGCG ACTGA GTTGC TTGAG CAGGT GCTGC                 GTTGG TGAAT CCCGG
         11111 11111 11111 11111 11111 11111 11111 11111                 11111 11111 11111
B73/7-4  CCCAA GCCCC CTGCG ACTGA GTTGC TTGAG CAGGT GCTGC           11111 GTTGG TGAAT CgCGG
         11111 11111 11111 11111 11111 11111 11111 11111                 11111 11111 11111
XI12/8A  CCCAA GCCCC CTGCG ACTGA GTTGC TTGAG CAGGT GCTGC           11111 GTTGG TGAAT CCCGG 850                860                870                 880               890              900
XI12/8A  CGCCC TGTTC TTTAT GTTGG CGGTG CGTGC GCAGC ATCTG GTGAG GAGTT GCGAC GCTTT

W22/1A   CGCCC TGTTC TTTAT GTTGG CGGTG           GCAGC ATCTG GTGAG GAGTT GCGAC GCTTT
         11111 11111 11111 11111 11111     11111 11111 11111 11111 11111 11111 11111
B73/7-4  CGCCC TGTTC TTTAT       CGGTG           GCAGC ATCTG GTGAG GAGTT GCGAC GCTTT
         11111 11111 11111       11111     11111 11111 11111 11111 11111 11111 11111
XI12/8A  CGCCC TGTTC TTTAT GTTGG CGGTG           GCAGC ATCTG GTGAG GAGTT GCGAC GCTTT
```

FIG. 7F

|  |  | 910 | 920 | 930 | 940 | 950 | 960 |
|---|---|---|---|---|---|---|---|
| XI12/8A |  | GTGGA | CTGGA | ATCCC | GGTCA | CAACT | ACTCT | TATGG | GCCTC | GGCAA | CTTCC | CCAGC |
| W22/1A | GTGGA | GCTGA | CTGGA | ATCCC | GGTCA | CAACT | ACTCT | TATGG | GCCTC | GGCAA | CTTCC | CCAGC |
|  | 11111 | 11111 | 11111 | 11111 | 11111 | 11111 | 11111 | 11111 | 11111 | 11111 | 11111 |
| B73/7-4 | GTGGA | GCTGA | CTGGA | ATCCC | GGTCA | CAACT | ACTCT | TATGG | GCCTC | GGCAA | CTTCC | CCAGC |
|  | 11111 | 11111 | 11111 | 11111 | 11111 | 11111 | 11111 | 11111 | 11111 | 11111 | 11111 |
| XI12/8A | GTGGA | GCTGA | CTGGA | ATCCC | GGTCA | CAACT | ACTCT | TATGG | GCCTC | GGCAA | CTTCC | CCAGC |

|  |  | 970 | 980 | 990 | 1000 | 1010 | 1020 |
|---|---|---|---|---|---|---|---|
| XI12/8A | GACGA | CCCAC | TGTCT | CTGCG | CATGC | TAGGT | ATGCA | TGGCA | CGGTG | TATGC | AAATT | ATGCA |
| W22/1A | GACGA | CCCAC | TGTCT | CTGCG | CATGC | TAGGT | ATGCA | TGGCA | CGGTG | TATGC | AAATT | ATGCA |
|  | 11111 | 11111 | 11111 | 11111 | 11111 | 11111 | 11111 | 11111 | 11111 | 11111 | 11111 |
| B73/7-4 | GACGA | CCCAC | TGTCT | CTGCG | CATGC | TAGGT | ATGCA |  | CGGTG | TATGC | AAATT | ATGCA |
|  | 11111 | 11111 | 11111 | 11111 | 11111 | 11111 |  | 11111 | 11111 | 11111 | 11111 |
| XI12/8A | GACGA | CCCAC | TGTCT | CTGCG | CATGC | TAGGT | ATGCA | TGGCA | CGGTG | TATGC | AAATT | ATGCA |

|  |  | 1030 | 1040 | 1050 | 1060 | 1070 | 1080 |
|---|---|---|---|---|---|---|---|
| XI12/8A | GTGGA | TAAGG | CCGAT | CTGTT | GCTTG | CACTT | GGTGT | GCGGT | TTGAT | GATCG | TGTGA | CAGGG |
| W22/1A | GTGGA | TAAGG | CCGAT | CTGTT | GCTTG | CACTT | GGTGT | GCGGT | TTGAT | GATCG | TGTGA | CAGGG |
|  | 11111 | 11111 | 11111 | 11111 | 11111 | 11111 | 11111 | 11111 | 11111 | 11111 | 11111 |
| B73/7-4 | GTGGA | TAAGG | CCGAT | CTGTT | GCTTG | CACTT | GGTGT | GCGGT | TTGAT | GATCG |  | CAGGG |
|  | 11111 | 11111 | 11111 | 11111 | 11111 | 11111 | 11111 | 11111 | 11111 |  | 11111 |
| XI12/8A | GTGGA | TAAGG | CCGAT | CTGTT | GCTTG | CACTT | GGTGT | GCGGT | TTGAT | GATCG | TGTGA | CAGGG |

FIG. 7G

```
                     1090       1100       1110       1120       1130       1140
XI12/8A        AAGAT TGAGG CTTTT GCAAG CAGGG CTAAG ATTGT GCACG TTGAT ATTGA TCCGG CTGAG
W22/1A         AAGAT TGAGG CTTTT GCAAG CAGGG CTAAG ATTGT GCACG TTGAT ATTGA TCCGG CTGAG
               11111 11111 11111 11111 11111 11111 11111 11111 11111 11111 11111 11111
B73/7-4        AAGAT TGAGG CTTTT GCAAG CAGGG CTAAG ATTGT GCACG TTGAT ATTGA TCCGG CTGAG
               11111 11111 11111 11111 11111 11111 11111 11111 11111 11111 11111 11111
XI12/8A        AAGAT TGAGG CTTTT GCAAG CAGGG CTAAG ATTGT GCACG TTGAT ATTGA TCCGG CTGAG 1150       1160       1170       1180       1190       1200
XI12/8A        ATTGG CAAGA ACAAG CAGCC ACATG TGTCC ATCTG TGCAG ATGTT AAGCT TGCTT TGCAG
W22/1A         ATTGG CAAGA ACAAG CAGCC ACATG TGTCC ATCTG TGCAG ATGTT AAGCT TGCTT TGCAG
               11111 11111 11111 11111 11111 11111 11111 11111 11111 11111 11111 11111
B73/7-4        ATTGG CAAGA ACAAG CAGCC ACATG TGTCC ATCTG TGCAG ATGTT AAGCT TGCTT TGCAG
               11111 11111 11111 11111 11111 11111 11111 11111 11111 11111 11111 11111
XI12/8A        ATTGG CAAGA ACAAG CAGCC ACATG TGTCC ATCTG TGCAG ATGTT AAGCT TGCTT TGCAG 1210       1220       1230       1240       1250       1260
XI12/8A        GGCAT GAATG CTCTT CTTGA AGGAA GCACA TCAAA GAAGA GCTTT GACTT TGGCT CATGG
W22/1A         GGCAT GAATG CTCTT CTTGA AGGAA GCACA TCAAA GAAGA GCTTT GACTT TGGCT CATGG
               11111 11111 11111 11111 11111 11111 11111 11111 11111 11111 11111 11111
B73/7-4        GGCAT GAATG CTCTT CTTGA AGGAA GCACA TCAAA GAAGA GCTTT GACTT TGGCT CATGG
               11111 11111 11111 11111 11111 11111 11111 11111 11111 11111 11111 11111
XI12/8A        GGCAT GAATG CTCTT CTTGA AGGAA GCACA TCAAA GAAGA GCTTT GACTT TGGCT CATGG
```

FIG. 7H

```
                     1270        1280        1290        1300        1310        1320
XI12/8A       AACGA TGAGT TGGAT CAGCA GAAGA GGGAA TTCCC CCTTG GGTAT AAAAC ATCTA ATGAG
W22/1A        AACGA TGAGT TGGAT CAGCA GAAGA GGGAA TTCCC CCTTG GGTAT AAAAC ATCTA ATGAG
              11111 11111 11111 11111 11111 11111 11111 11111 11111 11111 11111 11111
B73/65        AACGA TGAGT TGGAT CAGCA GAAGA GGGAA TTCCC CCTTG GGTAT AAAAC ATCTA ATGAG
              11111 11111 11111 11111 11111 11111 11111 11111 11111 11111 11111 11111
XI12/8A       AACGA TGAGT TGGAT CAGCA GAAGA GGGAA TTCCC CCTTG GGTAT AAAAC ATCTA ATGAG 1330        1340        1350        1360        1370        1380
XI12/8A       GAGAT CCAGC CACAA TATGC TATTC AGGTT CTTGA TGAGC TGACG AAAGG CGAGG CCATC
W22/1A        GAGAT CCAGC CACAA TATGC TATTC AGGTT CTTGA TGAGC TGACG AAAGG CGAGG CCATC
              11111 11111 11111 11111 11111 11111 11111 11111 11111 11111 11111 11111
B73/7-4       GAGAT CCAGC CACAA TATGC TATTC AGGTT CTTGA TGAGC TGACG AAAGG CGAGG CCATC
              11111 11111 11111 11111 11111 11111 11111 11111 11111 11111 11111 11111
XI12/8A       GAGAT CCAGC CACAA TATGC TATTC AGGTT CTTGA TGAGC TGACG AAAGG CGAGG CCATC 1390        1400        1410        1420        1430        1440
              ATCGG CACAG GTGTT GGGCA GCACC AGATG TGGGC GGCAC AGTAC TACAC TTACA AGCGG
W22/1A        ATCGG CACAG GTGTT GGGCA GCACC AGATG TGGGC GGCAC AGTAC TACAC TTACA AGCGG
              11111 11111 11111 11111 11111 11111 11111 11111 11111 11111 11111 11111
B73/7-4       ATCGG CACAG GTGTT GGGCA GCACC AGATG TGGGC GGCAC AGTAC TACAC TTACA AGCGG
              11111 11111 11111 11111 11111 11111 11111 11111 11111 11111 11111 11111
XI12/8A       ATCGG CACAG GTGTT GGGCA GCACC AGATG TGGGC GGCAC AGTAC TACAC TTACA AGCGG
```

FIG. 7I

```
                  1450        1460        1470        1480        1490        1500
XI12/8A    CCAAG GCAGT GGTTG TCTTC AGCTG GTCTT GGGGC TATGG GATTT GGTTT GCCGG CTGCT
W22/1A     CCAAG GCAGT GGTTG TCTTC AGCTG GTCTT GGGGC TATGG GATTT GGTTT GCCGG CTGCT
           11111 11111 11111 11111 11111 11111 11111 11111 11111 11111 11111 11111
B73/7-4    CCAAG GCAGT GGTTG TCTTC AGCTG GTCTT GGGGC TATGG GATTT GGTTT GCCGG CTGCT
           11111 11111 11111 11111 11111 11111 11111 11111 11111 11111 11111 11111
XI12/8A    CCAAG GCAGT GGTTG TCTTC AGCTG GTCTT GGGGC TATGG GATTT GGTTT GCCGG CTGCT 1510        1520        1530        1540        1550        1560
XI12/8A    GCTGG TGCTT CTGTG GCCAA CCCAG GTGTT ACTGT TGTTG ACATC GATGG AGATG GTAGC
W22/1A     GCTGG TGCTT CTGTG GCaAA CCCAG GTGTT ACTGT TGTTG ACATC GATGG AGATG GTAGC
           11111 11111 11111 11111 11111 1111  11111 11111 11111 11111 11111 11111
                                             ^
B73/7-4    GCTGG TGCTT CTGTG GCaAA CCCAG GTGTc ACTGT TGTTG ACATC GATGG AGATG GTAGC
           11111 11111 11111 11 11 11111 1111  11111 11111 11111 11111 11111 11111
XI12/8A    GCTGG TGCTT CTGTG GCCAA CCCAG GTGTT ACTGT TGTTG ACATC GATGG AGATG GTAGC 1570        1580        1590        1600        1610        1620
XI12/8A    TTTCT CATGA ACGTT CAGGA GCTAG CTATG ATCCG AATTG AGAAC CTCCC GGTGA AGGTC
W22/1A     TTTCT CATGA ACGTT CAGGA GCTAG CTATG ATCCG AATTG AGAAC CTCCC GGTGA AGGTC
           11111 11111 11111 11111 11111 11111 11111 11111 11111 11111 11111 11111
                                                                       ^
B73/7-4    TTTCT CATGA ACGTT CAGGA GCTAG CTATG ATCCG AATTG AGAAC CTCCC aGTGA AGGTC
           11111 11111 11111 11111 11111 11111 11111 11111 11111 11111 1111  11111
XI12/8A    TTTCT CATGA ACGTT CAGGA GCTAG CTATG ATCCG AATTG AGAAC CTCCC GGTGA AGGTC
```

FIG. 7J

```
                1630  1640  1650  1660  1670  1680
XI12/8A   TTTGT GCTAA ACAAC CAGCA CCTGG GGATG GTGGT GCAGT GGGAG GACAG GTTCT ATAAG
W22/1A    TTTGT GCTAA ACAAC CAGCA CCTGG GGATG GTGGT GCAGT GGGAG GACAG GTTCT ATAAG
          11111 11111 11111 11111 11111 1111  11111 11111     11111 11111 11111
B73/7-4   TTTGT GCTAA ACAAC CAGCA CCTGG GGATG GTGGT GCAGT tGGAG GACAG GTTCT ATAAG
          11111 11111 11111 11111 11111 1111  11111 11111     11111 11111 11111
                                                       #
XI12/8A   TTTGT GCTAA ACAAC CAGCA CCTGG GGATG GTGGT GCAGT GGGAG GACAG GTTCT ATAAG 1690  1700  1710  1720  1730  1740
XI12/8A   GCCAA CAGAG CGCAC ACATA CTTGG GAAAC CCAGA GAATG AAAGT GAGAT ATATC CAGAT
W22/1A    GCCAA CAGAG CGCAC ACATA CTTGG GAAAC CCAGA GAATG AAAGT GAGAT ATATC CAGAT
          11111 11111 11111 11111 11111 11111 11111 11111 11111 11111 11111 11111
B73/7-4   GCCAA CAGAG CGCAC ACATA CTTGG GAAAC CCAGA GAATG AAAGT GAGAT ATATC CAGAT
          11111 11111 11111 11111 11111 11111 11111 11111 11111 11111 11111 11111
XI12/8A   GCCAA CAGAG CGCAC ACATA CTTGG GAAAC CCAGA GAATG AAAGT GAGAT ATATC CAGAT 1750  1760  1770  1780  1790  1800
XI12/8A   TTCGT GACGA TCGCC AAAGG GTTCA ACATT CCAGC GGTCC GTGTG ACAAA GAAGA ACGAA
W22/1A    TTCGT GACGA TCGCC AAAGG GTTCA ACATT CCAGC GGTCC GTGTG ACAAA GAAGA ACGAA
          11111 11111 11111 11111 11111 11111 11111 11111 11111 11111 11111 11111
B73/7-4   TTCGT GACGA TCGCC AAAGG GTTCA ACATT CCAGC GGTCC GTGTG ACAAA GAAGA ACGAA
          11111 11111 11111 11111 11111 11111 11111 11111 11111 11111 11111 11111
XI12/8A   TTCGT GACGA TCGCC AAAGG GTTCA ACATT CCAGC GGTCC GTGTG ACAAA GAAGA ACGAA
```

FIG. 7K

```
              1810        1820        1830        1840        1850        1860
XI12/8A  GTCCG CGCAG CGATA AAGAA GATGC TCGAG ACTCC AGGGC CGTAC CTCTT GGATA TAATC

W22/1A   GTCCG CGCAG CGATA AAGAA GATGC TCGAG ACTCC AGGGC CGTAC CTCTT GGATA TAATC
         11111 11111 11111 11111 11111 11111 11111 11111 11111 11111 11111 11111
B73/7-4  GTCCG CGCAG CGATA AAGAA GATGC TCGAG ACTCC AGGGC CGTAC CTCTT GGATA TAATC
         11111 11111 11111 11111 11111 11111 11111 11111 11111 11111 11111 11111
XI12/8A  GTCCG CGCAG CGATA AAGAA GATGC TCGAG ACTCC AGGGC CGTAC CTCTT GGATA TAATC 1870        1880        1890        1900        1910        1920
XI12/8A  GTCCC ACACC AGGAG CATGT GTTGC CTATG ATCCC TAATG GTGGG GCTTT CAAGG ATATG

W22/1A   GTCCC ACACC AGGAG CATGT GTTGC CTATG ATCCC TAgTG GTGGG GCTTT CAAGG ATATG
         11111 11111 11111 11111 11111 11111 11111 11111 11111 11111 11111 11111
B73/7-4  GTCCC ACACC AGGAG CATGT GTTGC CTATG ATCCC TAgTG GTGGG GCTTT CAAGG ATATG
         11111 11111 11111 11111 11111 11111 11 11 11 11 11111 11111 11111 11111
XI12/8A  GTCCC ACACC AGGAG CATGT GTTGC CTATG ATCCC TAATG GTGGG GCTTT CAAGG ATATG 1930        1940        1950        1960
XI12/8A  ATCCT GGATG GTGAT GGCAG GACTG TGTAC TGATC TAAAA TCCAG CAAG

W22/1A   ATCCT GGATG GTGAT GGCAG GACTG TGTAC TGATC TAAAA TCCAG CAAG>
         11111 11111 11111 11111 11111 11111 11111 11111 11111 1111
B73/7-4  ATCCT GGATG GTGAT GGCAG GACTG TGTAC TGATC TAAAA TCCAG CAAG>
         11111 11111 11111 11111 11111 11111 11111 11111 11111 1111
XI12/8A  ATCCT GGATG GTGAT GGCAG GACTG TGTAC TGATC TAAAA TCCAG CAAG
```

FIG. 8A

```
                      10          20          30          40          50          60
XI12/8A       MATAA AASTA LTGAT TAAPK ARRRA HLLAT RRALA APIRC SAASP AMPMA PPATP LRPWG
W22/1A        MATAA AASTA LTGAT TAAPK ARRRA HLLAT RRALA APIRC SAASP AMPMA PPATP LRPWG
              11111 11111 111 1 11111 11111 11111 11111 11111 11111 11111 11111 11111
B73/7-4       MATAA AASTA LTGAT TAAPK ARRRA HLLAT RRALA APIRC SAASP AMPMA PPATP LRPWG
              11111 11111 11111 11111 11111 11111 11111 11111 11111 11111 11111 11111
XI12/8A       MATAA AASTA LTGAT TAAPK ARRRA HLLAT RRALA APIRC SAASP AMPMA PPATP LRPWG 70          80          90         100         110         120
XI12/8A       PTDPR KGADI LVESL ERCGV RDVFA YPGGA SMEIH QALTR SPVIA NHLFR HEQGE AFAAS
W22/1A        PTDPR KGADI LVESL ERCGV RDVFA YPGGA SMEIH QALTR SPVIA NHLFR HEQGE AFAAS
              11 11 11111 11111 11111 11111 11111 11111 11111 11111 11111 11111 11111
                *
B73/7-4       PTePR KGADI LVESL ERCGV RDVFA YPGGA SMEIH QALTR SPVIA NHLFR HEQGE AFAAS
              11 11 11111 11111 11111 11111 11111 11111 11111 11111 11111 11111 11111
XI12/8A       PTDPR KGADI LVESL ERCGV RDVFA YPGGA SMEIH QALTR SPVIA NHLFR HEQGE AFAAS 130         140         150         160         170         180
XI12/8A       GYARS SGRVG VCIAT SGPGA TNLVS ALADA LLDSV PMVAI TGQVP RRMIG TDAFQ ETPIV
W22/1A        GYARS SGRVG VCIAT SGPGA TNLVS ALADA LLDSV PMVAI TGQVP RRMIG TDAFQ ETPIV
              11111 11111 11111 11111 11111 11111 11111 11111 11111 11111 11111 11111
B73/7-4       GYARS SGRVG VCIAT SGPGA TNLVS ALADA LLDSV PMVAI TGQVP RRMIG TDAFQ ETPIV
              11111 11111 11111 11111 11111 11111 11111 11111 11111 11111 11111 11111
XI12/8A       GYARS SGRVG VCIAT SGPGA TNLVS ALADA LLDSV PMVAI TGQVP RRMIG TDAFQ ETPIV
```

FIG. 8B

```
              190         200         210         220         230         240
XI12/8A       EVTRS ITKHN YLVLD VDDIP RVVQE AFFLA SSGRP GPVLV DIPKD IQQQM AVPVW DKPMS
W22/1A        EVTRS ITKHN YLVLD VDDIP RVVQE AFFLA SSGRP GPVLV DIPKD IQQQM AVPVW DKPMS
              11111 11111 11111 11111 11111 11111 11111 11111 11111 11111 11111 11111
B73/7-4       EVTRS ITKHN YLVLD VDDIP RVVQE AFFLA SSGRP GPVLV DIPKD IQQQM AVPVW DKPMS
              11111 11111 11111 11111 11111 11111 11111 11111 11111 11111 11111 11111
XI12/8A       EVTRS ITKHN YLVLD VDDIP RVVQE AFFLA SSGRP GPVLV DIPKD IQQQM AVPVW DKPMS 250         260         270         280         290         300
XI12/8A       LPGYI ARLPK PPATE LLEQV LRLVG ESRRP VLYVG GGCAA SGEEL RRFVE LTGIP VTTTL
W22/1A        LPGYI ARLPK PPATE LLEQV LRLVG ESRRP VLYVG GGCAA SGEEL RRFVE LTGIP VTTTL
              11111 11111 11111 11111 11111 11111 11111 11111 11111 11111 11111 11111
B73/7-4       LPGYI ARLPK PPATE LLEQV LRLVG ESRRP VLYVG GGCAA SGEEL RRFVE LTGIP VTTTL
              11111 11111 11111 11111 11111 11111 11111 11111 11111 11111 11111 11111
XI12/8A       LPGYI ARLPK PPATE LLEQV LRLVG ESRRP VLYVG GGCAA SGEEL RRFVE LTGIP VTTTL 310         320         330         340         350         360
XI12/8A       MGLGN FPSDD PLSLR MLGMH GTVYA NYAVD KADLL LALGV RFDDR VTGKI EAFAS RAKIV
W22/1A        MGLGN FPSDD PLSLR MLGMH GTVYA NYAVD KADLL LALGV RFDDR VTGKI EAFAS RAKIV
              11111 11111 11111 11111 11111 11111 11111 11111 11121 12111 11211 11111
B73/7-4       MGLGN FPSDD PLSLR MLGMH GTVYA NYAVD KADLL LALGV RFDDR VTGKI EAFAS RAKIV
              11111 11111 11111 11111 11111 11111 11111 11111 11111 11111 11111 11111
XI12/8A       MGLGN FPSDD PLSLR MLGMH GTVYA NYAVD KADLL LALGV RFDDR VTGKI EAFAS RAKIV
```

FIG. 8C

```
                370         380         390         400         410         420
XI12/8A   HVDID PAEIG KNKQP HVSIC ADVKL ALQGM NALLE GSTSK KSFDF GSWND ELDQQ KREFP
W22/1A    HVDID PAEIG KNKQP HVSIC ADVKL ALQGM NALLE GSTSK KSFDF GSWND ELDQQ KREFP
          11111 11111 11111 11111 11111 11111 11111 11111 11111 11111 11111 11111
B73/7-4   HVDID PAEIG KNKQP HVSIC ADVKL ALQGM NALLE GSTSK KSFDF GSWND ELDQQ KREFP
          11111 11111 11111 11111 11111 11111 11111 11111 11111 11111 11111 11111
XI12/8A   HVDID PAEIG KNKQP HVSIC ADVKL ALQGM NALLE GSTSK KSFDF GSWND ELDQQ KREFP 430         440         450         460         470         480
XI12/8A   LGYKT SNEEI QPQYA IQVLD ELTKG EAIIG TGVGQ HQMWA AQYYT YKRPR QWLSS AGLGA
W22/1A    LGYKT SNEEI QPQYA IQVLD ELTKG EAIIG TGVGQ HQMWA AQYYT YKRPR QWLSS AGLGA
          11111 11111 11111 11111 11111 11111 11111 11111 11111 11111 11111 11111
B73/7-4   LGYKT SNEEI QPQYA IQVLD ELTKG EAIIG TGVGQ HQMWA AQYYT YKRPR QWLSS AGLGA
          11111 11111 11111 11111 11111 11111 11111 11111 11111 11111 11111 11111
XI12/8A   LGYKT SNEEI QPQYA IQVLD ELTKG EAIIG TGVGQ HQMWA AQYYT YKRPR QWLSS AGLGA 490         500         510         520         530         540
XI12/8A   MGFGL PAAAG ASVAN PGVTV VDIDG DGSFL MNVQE LAMIR IENLP VKVFV LNNQH LGMVV
W22/1A    MGFGL PAAAG ASVAN PGVTV VDIDG DGSFL MNVQE LAMIR IENLP VKVFV LNNQH LGMVV
          11111 11111 11111 11111 11111 11111 11111 11111 11111 11111 11111 11111
B73/7-4   MGFGL PAAAG ASVAN PGVTV VDIDG DGSFL MNVQE LAMIR IENLP VKVFV LNNQH LGMVV
          11111 11111 11111 11111 11111 11111 11111 11111 11111 11111 11111 11111
XI12/8A   MGFGL PAAAG ASVAN PGVTV VDIDG DGSFL MNVQE LAMIR IENLP VKVFV LNNQH LGMVV
```

FIG. 8D

```
                550        560        570        580        590        600
XI12/8A    QWEDR FYKAN RAHTY LGNPE NESEI YPDFV TIAKG FNIPA VRVTK KNEVR AAIKK MLETP
                  *
W22/1A     1 111 11111 11111 11111 11111 11111 11111 11111 11111 11111 11111 11111
B73/7-4    QLEDR FYKAN RAHTY LGNPE NESEI YPDFV TIAKG FNIPA VRVTK KNEVR AAIKK MLETP
           1 111 11111 11111 11111 11111 11111 11111 11111 11111 11111 11111 11111
XI12/8A    QWEDR FYKAN RAHTY LGNPE NESEI YPDFV TIAKG FNIPA VRVTK KNEVR AAIKK MLETP 610        620        630
XI12/8A    GPYLL DIIVP HQEHV LPMIP NGGAF KDMIL DGDGR TVY*
W22/1A     11111 11111 11111 11111    *
           GPYLL DIIVP HQEHV LPMIP sGGAF KDMIL DGDGR TVY>
B73/7-4    11111 11111 11111 11111 11111 11111 11111 111
           GPYLL DIIVP HQEHV LPMIP sGGAF KDMIL DGDGR TVY>
           11111 11111 11111 11111  111  11111 11111 111
XI12/8A    GPYLL DIIVP HQEHV LPMIP NGGAF KDMIL DGDGR TVY
```

IMIDAZOLINONE RESISTANT AHAS MUTANTS

This is a continuation-in-part of copending application(s) Ser. No. 07/737,851 filed on Jul. 31, 1991, the contents of which are incorporated herein by reference.

This invention relates to novel DNA sequences that encode novel variant forms of acetohydroxy acid synthase enzyme (hereinafter AHAS). The AHAS enzyme is a critical enzyme routinely produced in a variety of plants and a broad range of microorganisms. Normal AHAS function is inhibited by imidazolinone herbicides; however, new AHAS enzymes encoded by the mutant DNA sequences function normally catalytically even in the presence of imidazolinone herbicides and, therefore, confer herbicide resistance upon the plant or microorganism containing them.

The novel DNA sequences are derived from corn and have a substitution of an amino acid at position 621 of the normal AHAS sequence. This substitution in the AHAS gene sequence results in a fully functional enzyme, but renders the enzyme specifically resistant to inhibition by a variety of imidazolinone herbicides. The availability of these variant sequences provides a tool for transformation of different crop plants to imidazolinone herbicide resistance, as well as providing novel selectable markers for use in other types of genetic transformation experiments.

BACKGROUND OF THE INVENTION

The use of herbicides in agriculture is now widespread. Although there are a large number of available compounds which effectively destroy weeds, not all herbicides are capable of selectively targeting the undersirable plants over crop plants, as well as being non-toxic to animals. Often, it is necessary to settle for compounds which are simply less toxic to crop plants than to weeds. In order to overcome this problem, development of herbicide resistant crop plants has become a major focus of agricultural research.

An important aspect of development of herbicide-resistance is an understanding of the herbicide target, and then manipulating the affected biochemical pathway in the crop plant so that the inhibitory effect is avoided while the plant retains normal biological function. One of the first discoveries of the biochemical mechanism of herbicides related to a series of structurally unrelated herbicide compounds, the imidazolinones, the sulfonylureas and the triazolopyrimidines. It is now known (Shaner et al. *Plant Physiol.* 76: 545–546,1984; U.S. Pat. No. 4,761,373) that each of these herbicides inhibits plant growth by interference with an essential enzyme required for plant growth, acetohydroxyacid synthase (AHAS; also referred to as acetolacetate synthase, or ALS). AHAS is required for the synthesis of the amino acids isoleucine, leucine and valine.

The AHAS enzyme is known to be present throughout higher plants, as well as being found in a variety of microorganisms, such as the yeast *Saccharomyces cerevisiae*, and the enteric bacteria, *Escherichia coli* and *Salmonella typhimurium*. The genetic basis for the production of normal AHAS in a number of these species has also been well characterized. For example, in both *E. coli* and *S. typhimurium* three isozymes of AHAS exist; two of these are sensitive to herbicides while a third is not. Each of these isozymes possesses one large and one small protein subunit; and map to the IlvIH, IlvGM and IlvBN operons. In yeast, the single AHAS isozyme has been mapped to the ILV2 locus. In each case, sensitive and resistant forms have been identified and sequences of the various alleles have been determined (Friden et. al., *Nucl. Acid Res.* 13: 3979–3993, 1985; Lawther et al., *PNAS USA* 78: 922–928, 1982; Squires et al., *Nucl. Acids Res* 811: 5299–5313, 1983; Wek et al; *Nucl. Acids Res* 13: 4011–4027, 1985; Falco and Dumas, *Genetics* 109, 21–35, 985; Falco et al, *Nucl. Acids Res* 13: 4011–4027, 1985).

In tobacco, AHAS function is encoded by two unlinked genes, SuRA and SuRB. There is substantial identity between the two genes, both at the nucleotide level and amino acid level in the mature protein, although the N-terminal, putative transit region differs more substantially (Lee et al. *EMBO J.* 7: 1241–1248, 1988). Arabidopsis, on the other hand, has a single AHAS gene, which has also been completely sequenced (Mazur et al., *Plant Physiol.* 85: 1110–1117, 1987). Comparisons among sequences of the AHAS genes in higher plants indicates a high level of conservation of certain regions of the sequence; specifically, there are at least 10 regions of sequence conservation. It has previously been assumed that these conserved regions are critical to the function of the enzyme, and that retention of that function is dependent upon substantial sequence conservation.

It has been recently reported (U.S. Pat. No. 5,013,659) that mutants exhibiting herbicide resistance possess mutations in at least one amino acid in one or more of these conserved regions. In particular, substitution of certain amino acids for the wild type amino acid at these specific sites in the AHAS protein sequence have been shown to be tolerated, and indeed result in herbicide resistance of the plant possessing this mutation, while retaining catalytic function. The mutations described therein encode either cross resistance for imidazolinones and sulfonylureas or sulfonylurea-specific resistance, but no imidazolinone-specific mutations were disclosed. These mutations have been shown to occur at both the SuRA and SuRB loci in tobacco; similar mutations have been isolated in Arabidopsis and yeast.

Imidazolinone-specific resistance has been reported elsewhere in a number of plants. U.S. Pat. No. 4,761,373 generally described an altered AHAS as a basis of herbicide resistance in plants, and specifically disclosed certain imidazolinone resistant corn lines. Haughn et al. (*Mol. Gen. Genet.* 211: 266–271, 1988) disclosed the occurrence of a similar phenotype in Arabidopsis. Sathasivan et al. (*Nucl. Acid Res.* 18: 2188, 1990) identified the imidazolinone-specific resistance in Arabidopsis as being based on a mutation at position 653 in the normal AHAS sequence. In accordance with the present invention, a gene encoding imidazolinone-specific resistance in a monocot has now been isolated and determined to be associated with a single amino acid substitution in a wild-type monocot AHAS amino acid sequence.

SUMMARY OF THE INVENTION

The present invention provides novel nucleic acid sequences encoding functional monocot AHAS enzymes insensitive to imidazolinone herbicides. The sequences in question comprise a mutation in the codon encoding the amino acid serine at position 621 in the corn (maize) AHAS sequence, or in the corresponding position in other monocot sequences. Other monocots, such as wheat, are also known to exhibit imidazolinone specific mutations (e.g., ATCC Nos. 40994-97). In corn, the wild type sequence has a serine at this position. In a preferred embodiment, the substitution is asparagine for serine, but alternate substitutions for serine include aspartic acid, glutamic acid, glutamine and tryptophane. Although the claimed sequences are originally derived from monocots, the novel sequences are useful in methods for producing imidazolinone resistant cells in any type of plant, said methods comprising transforming a target plant cell with one or more of the altered sequences provided herein. Alternatively, mutagenesis is utilized to create mutants in plant cells or seeds containing a nucleic acid sequence encoding an imidazolinone insensitive AHAS. In the case of mutant plant cells isolated in tissue culture, plants which possess the imidazolinone resistant or insensitive trait are then regenerated. The invention thus also encompasses plant cells, bacterial cells, fungal cells, plant tissue cultures, adult plants, and plant seeds that possess a mutant nucleic acid sequence and which express functional imidazolinone resistant AHAS enzymes.

The availability of these novel herbicide resistant plants enables new methods of growing crop plants in the presence of imidazolinones. Instead of growing non-resistant plants, fields may be planted with the resistant plants produced by mutation or by transformation with the mutant sequences of the present invention, and the field routinely treated with imidazolinones, with no resulting damage to crop plants.

The mutant nucleic acids of the present invention also provide novel selectable markers for use in transformation experiments. The nucleic acid sequence encoding a resistant AHAS is linked to a second gene prior to transfer to a host cell, and the entire construct transformed into the host. Putative transformed cells are then grown in culture in the presence of inhibitory amounts of herbicide; surviving cells will have a high probability of having successfully acquired the second gene of interest. Alternately, the resistant AHAS gene can be cotransformed on an independent plasmid with the gene of interest, whereby about 50% of all transformants can be expected to have received both genes.

The following definitions should be understood to apply throughout the specification and claims. A "functional" or "normal" AHAS enzyme is one which is capable of catalyzing the first step in the pathway for synthesis of the essential amino acids isoleucine, leucine and valine. A "wild-type" AHAS sequence is a sequence present in an imidazolinone sensitive member of a given species. A "resistant" plant is one which produces a mutant but functional AHAS enzyme, and which is capable of reaching maturity when grown in the presence of normally inhibitory levels of imidazolinone. The term "resistant", as used herein, is also intended to encompass "tolerant" plants, i.e., those plants which phenotypically evidence adverse, but not lethal, reactions to the imidazolinone.

BRIEF DESCRIPTION OF THE FIGURES

FIGS. 6A–6I: Nucleotide and deduced amino acid sequences of the XI12/8A mutant AHAS gene.

FIGS. 7A–7K: Nucleotide sequence alignment of XI12/8A, B73/7-4 and W22/1A als2 genes. (*) marks the base change causing the mutation at position 621, (#) differences from the B73/7-4 sequence and (>) represents silent changes.

FIGS. 8A–8D: Amino acid sequences and alignment of XI12/BA, B73/7-4 and W22/1A als2 genes. (*) marks the mutation at position 621, (#) marks differences from the B73/7-4 sequence, and (>) represents silent changes.

DETAILED DESCRIPTION OF THE INVENTION

The gene of the present invention is isolatable from corn maize line XI12 (seed deposited with the American Type Culture Collection as Accession Number 75051), and has been inserted into plasmid pXI12/8A (deposited with the American Type Culture Collection as Accession Number 68643). It is also isolatable from any other imidazolinone-specific herbicide resistant mutant, such as the corn line QJ22 (deposited as a cell culture with the American Type Culture Collection as Accession Number 40129), or the various wheat plants (seed deposited with the American Type Collection as Accession Numbers 40994, 40995, 40996, or 40997). A genomic DNA library is created, for example, in phage EMBL-3 with DNA from one of the imidazolinone resistant mutants, preferably one which is homozygous for the resistance trait, and is screened with a nucleic acid probe comprising all or a part of a wild-type AHAS sequence.

In maize, the AHAS gene is found at two loci, als1 and als2 (Burr and Burr, Trends in Genetics 7: 55–61, 1991); the homology between the two loci is 95% at the nucleotide level. The mutation in XI12 is mapped to locus als2 on chromosome 5, whereas the nonmutant gene is mapped to locus als1 on chromosome 4 (Newhouse et al., "Imidazolinone-resistant crops". In The Imidazolinone Herbicides, Shaner and O'Connor (Eds.), CRC Press, Boca Raton, Fla., in Press) Southern analysis identifies some clones containing the mutant als2 gene, and some containing the non-mutant als1 gene. Both types are subcloned into sequencing vectors, and sequenced by the dideoxy sequencing method.

Figure 5:
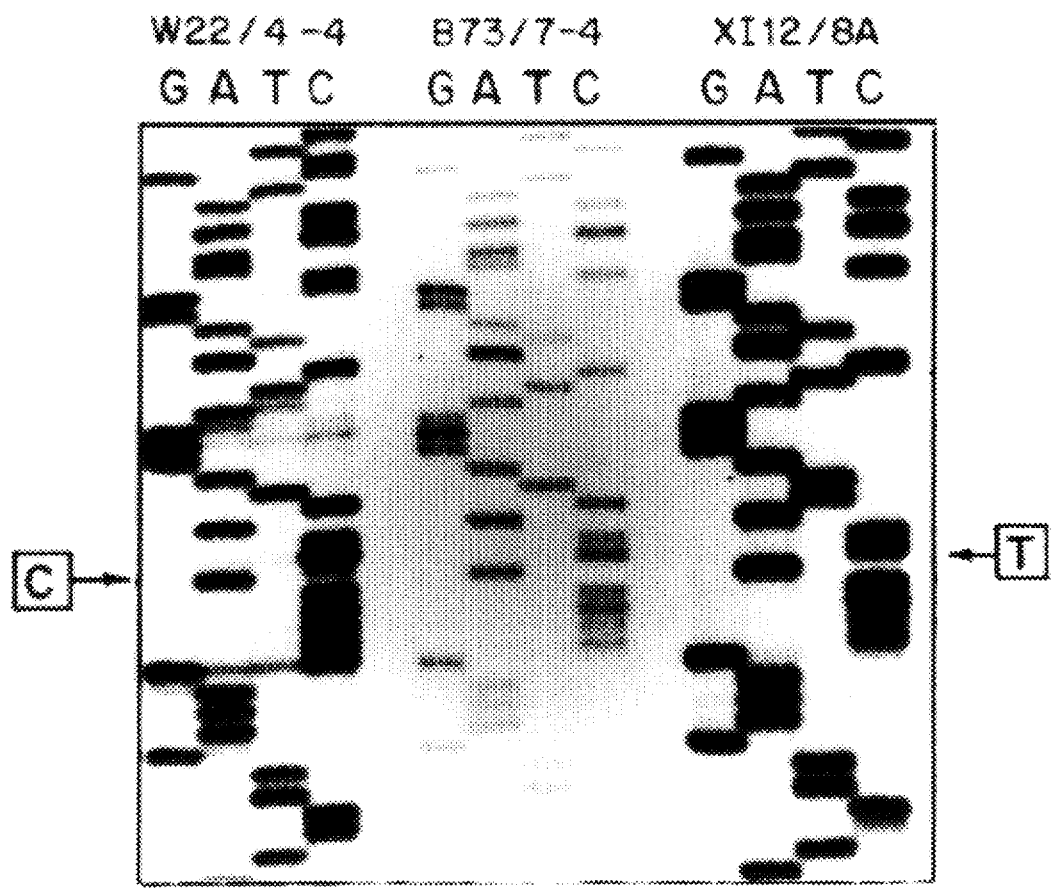

Sequencing and comparison of wild type and mutant AHAS genes shows a difference of a single nucleotide in the codon encoding the amino acid at position 621 (FIG. 5). Specifically, the codon AGT encoding serine in the wild type is changed to AAT encoding asparagine in the mutant AHAS (FIG. 8). The mutant AHAS gene is otherwise similar to the wild type gene, encoding a protein having 638 amino acids, the first 40 of which constitute a transit peptide which is thought to be cleaved during transport into the chloroplast in vivo. The sequence of the als1 non-mutant gene from XI12 appears to be identical to the als1 gene from B73.

The mutant genes of the present invention confer resistance to imidazolinone herbicides, but not to sulfonylurea herbicides. Types of herbicides to which resistance is conferred are described for example in U.S. Pat. Nos. 4,188,487; 4,201,565; 4,221,586; 4,297,128; 4,554,013; 4,608,079; 4,638,068; 4,747,301; 4,650,514; 4,698,092; 4,701,208; 4,709,036; 4,752,323; 4,772,311; and 4,798,619.

It will be understood by those skilled in the art that the nucleic acid sequence depicted in FIG. 6 is not the only sequence which can be used to confer imidazolinone-specific resistance. Also contemplated are those nucleic acid sequences which encode an identical protein but which, because of the degeneracy of the genetic code, possess a different nucleotide sequence. The invention also encompasses genes encoding AHAS sequences in which the aforestated mutation is present, but which also encode one or more silent amino acid changes in portions of the molecule not involved with resistance or catalytic function. Also contemplated are gene sequences from other imidazolinone resistant monocots which have a mutation in the corresponding region of the sequences.

For example, alterations in the gene sequence which result in the production of a chemically equivalent amino acid at a given site are contemplated; thus, a codon for the amino acid alanine, a hydrophobic amino acid, can readily be substituted by a codon encoding another hydrophobic residue, such as glycine, or may be substituted with a more hydrophobic residue such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. The invention also encompasses chimaeric genes, in which the substituted portion of the corn AHAS gene is recombined with unaltered portions of the normal AHAS genes from other species. Thus, throughout the specification and claims, wherever the term "imidazolinone-specific resistant corn AHAS gene" is used, it is intended to cover each of these alternate embodiments as well as the sequence of FIG. 6.

Isolated AHAS DNA sequences of the present invention are useful to transform target crop plants, and thereby confer imidazolinone resistance. A broad range of techniques currently exist for achieving direct or indirect transformation of higher plants with exogenous DNA, and any method by which the novel sequence can be incorporated into the host genome, and stably inherited by its progeny, is contemplated by the present invention. The imidazolinone specific resistance trait is inherited as a single dominant nuclear gene. The level of imidazolinone resistance is increased when the gene is present in a homozygous state; such corn plants, for example, have a resistance level of about 1,000 times that of a non-resistant plant. Plants heterozygous for the trait, however, have a resistance of about 50-500 times that of a non-resistant plant.

Transformation of plant cells can be mediated by the use of vectors. A common method of achieving transformation is the use of *Agrobacterium tumefaciens* to introduce a foreign gene into the target plant cell. For example, the mutant AHAS sequence is inserted into a plasmid vector containing the flanking sequences in the Ti-plasmid T-DNA. The plasmid is then transformed into *E. coli*. A triparental mating among this strain, an Agrobacterium strain containing a disarmed Ti-plasmid containing the virulence functions needed to effect transfer of the AHAS containing T-DNA sequences into the target plant chromosome, and a second *E. coli* strain containing a plasmid having sequences necessary to mobilize transfer of the AHAS construct from *E. coli* to Agrobacterium is carried out. A recombinant Agrobacterium strain, containing the necessary sequences for plant transformation is used to infect leaf discs. Discs are grown on selection media and successfully transformed regenerants are identified. The recovered plants are resistant to the effects of herbicide when grown in its presence. Plant viruses also provide a possible means for transfer of exogenous DNA.

Direct uptake of plant cells can also be employed. Typically, protoplasts of the target plant are placed in culture in the presence of the DNA to be transferred, and an agent which promotes the uptake of DNA by protoplast. Useful agents in this regard are polyethylene glycol or calcium phosphate.

Alternatively, DNA uptake can be stimulated by electroporation. In this method, an electrical pulse is used to open temporary pores in a protoplast cell membrane, and DNA in the surrounding solution is then drawn into the cell through the pores. Similarly, microinjection can be employed to deliver the DNA directly into a cell, and preferably directly into the nucleus of the cell.

In each of the foregoing techniques, transformation occurs in a plant cell in culture. Subsequent to the transformation event, plant cells must be regenerated to whole plants. Techniques for the regeneration of mature plants from callus or protoplast culture are now well known for a large number of different species (see, e.g., *Handbook of Plant Cell Culture*, Vols. 1-5, 1983-1989 McMillan, N.Y.) Thus, once transformation has been achieved, it is within the knowledge in the art to regenerate mature plants from the transformed plant cells.

Alternate methods are also now available which do not necessarily require the use of isolated cells, and therefore, plant regeneration techniques, to achieve transformation. These are generally referred to as "ballistic" or "particle acceleration" methods, in which DNA coated metal particles are propelled into plant cells by either a gunpowder charge (Klein et al., *Nature* 327: 70-73, 1987) or electrical discharge (EPO 270 356). In this manner, plant cells in culture or plant reproductive organs or cells, e.g. pollen, can be stably transformed with the DNA sequence of interest.

In certain dicots and monocots direct uptake of DNA is the preferred method of transformation. For example, in corn, the cell wall of cultured cells is digested in a buffer with one or more cell wall degrading enzymes, such as cellulase, hemicellulase and pectinase, to isolate viable protoplasts. The protoplasts are washed several times to remove the enzymes, and mixed with a plasmid vector containing the gene of interest. The cells can be transformed with either PEG (e.g. 20% PEG 4000) or by electroporation. The protoplasts are placed on a nitrocellulose filter and cultured on a medium with embedded corn cells functioning as feeder cultures. After 2–4 weeks, the cultures in the nitrocellulose filter are placed on a medium containing about 0.32 μM of the imidazolinone and maintained in the medium for 1–2 months. The nitrocellulose filters with the plant cells are transferred to fresh medium with herbicides and nurse cells every two weeks. The untransformed cells cease growing and die after a few weeks.

The present invention can be applied to transformation of virtually any type of plant, both monocot and dicot. Among the crop plants for which transformation to herbicide resistance is contemplated are corn, wheat, rice, millet, oat, barley, sorghum, sunflower, sweet potato, alfalfa, sugar beet, Brassica species, tomato, pepper, soybean, tobacco, melon, squash, potato, peanut, pea, cotton, or cacao. The novel sequences may also be used to transform ornamental species, such as rose, and woody species, such as pine and poplar.

The novel sequences of the invention also are useful as selectable markers in plant genetics studies. For example, in plant transformation, sequences encoding imidazolinone resistance could be linked to a gene of interest which is to be used to transform a target imidazolinone sensitive plant cell. The construct comprising both the gene of interest and the imidazolinone resistant sequence are introduced into the plant cell, and the plant cells are then grown in the presence of an inhibitory amount of an imidazolinone. Alternately, the second gene of interest can be cotransformed, on a separate plasmid, into the host cells. Plant cells surviving such treatment presumably have acquired the resistance gene as well as the gene of interest, and therefore, only transformants survive the selection process with the herbicide. Confirmation of successful transformation and expression of both genes can be achieved by Southern hybridization of genomic DNA, by PCR or by observation of the phenotypic expression of the genes.

The invention is further illustrated by the following non-limiting examples.

EXAMPLES

1. Confirmation of Whole Plant Herbicide Resistance in XI12

XI12 plants are treated with herbicides at 10 days to the V3 leaf stage (4–5 leaves, of which 3 have visible ligules). Imazethapyr is applied at rates of 2000, 500, 250, 125 and 62.5 g/ha. Chlorsulfuron is applied at 32, 16, 8, 4 and 2 g/ha. Plants are treated postemergence at a spray volume of 400 l/ha. After spraying, plants are placed in the greenhouse for further observation.

XI12 plants are unaffected at all rates of imazethapyr treatment; however, no visible increased resistance to chlorsulfuron is noted. Thus, XI12 displays selective resistance to the imidazolinone at the whole plant level (See FIG. 1).

The resistance in XI12 is also shown to be inherited as a single dominant allele of a nuclear gene. Heterozygous resistant XI12 are selfed, and the selfed progeny segregate in the 3 resistant:1 susceptible ratio expected for a single dominant allele of a nuclear gene. In this study, the segregating seedlings are sprayed postemergence with lethal doses of imazethapyr (125 or 250 g/ha) following spraying protocols described above, to establish segregation for resistance.

2. AHAS Extraction

Seeds of XI12 are sown in soil in a greenhouse maintained at day/night temperature of 80° C. and 15 hour photoperiod. Plants are harvested two weeks after planting. The basal portion of the shoot is used for the extraction of AHAS. 5 g of the tissue is powdered in liquid nitrogen and then homogenized in AHAS assay buffer comprising 100 mM potassium phosphate buffer (pH 7.5) containing 10 mM pyruvate, 5 mM MgCl$_2$, 5 mM EDTA, 100 uM FAD (flavin adenine dinucleotide), 1 mM valine, 1 mM leucine, 10% glycerol and 10 mM cysteine. The homogenate is centrifuged at 10,000 rpm for 10 minutes and 3 ml of the supernatant are applied onto an equilibrated Bio-Rad Econo-Desalting column (10 DG) and eluted with 4 ml AHAS assay buffer.

AHAS activity is measured by estimation of the product, acetolactate, after conversion by decarboxylation in the presence of acid to acetoin. Standard reaction mixtures contain the enzyme in 50 mM potassium phosphate (pH 7.0) containing 100 mM sodium pyruvate, 10 mM MgCl$_2$, 1 mM thiamine pyrophosphate, 10 uM FAD, and appropriate concentrations of different inhibitors. This mixture is incubated at 37° C. for 1 to 3 hours depending upon the experiment. At the end of this incubation period, the reaction is stopped with the addition of H$_2$SO$_4$ to make a final concentration of 0.85% H$_2$SO$_4$ in the tube. The reaction product is allowed to decarboxylate at 60° C. for 15 minutes. The acetoin formed is determined by incubating with creatine (0.17%) and 1-naphthol (1.7% in 4N NaOH). The absorption of color complex formed is measured at 520 nm.

Figure 1A:
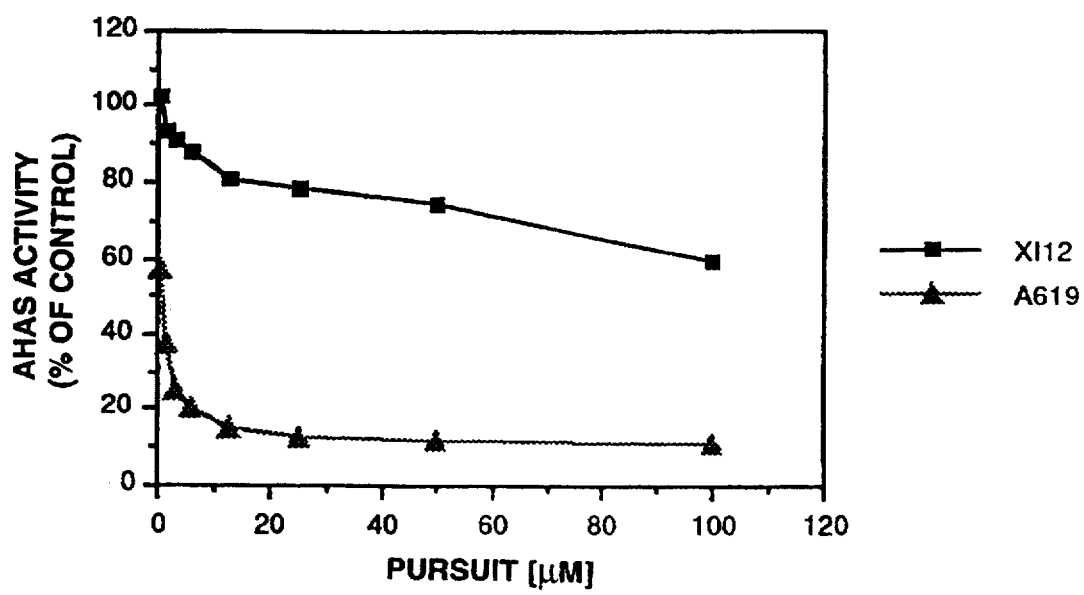
FIGS. 1A and 1B: AHAS enzyme activity in 10-day old maize seedlings (corn lines A619 or XI12) in the presence of imazethapyr (Pursuit™ A) or chlorsulfuron (Oust™ B). Herbicide resistant AHAS activity is calculated as percentage of AHAS activity in the absence of inhibitor. The standard error between experiments is 10%.
Figure 1B:
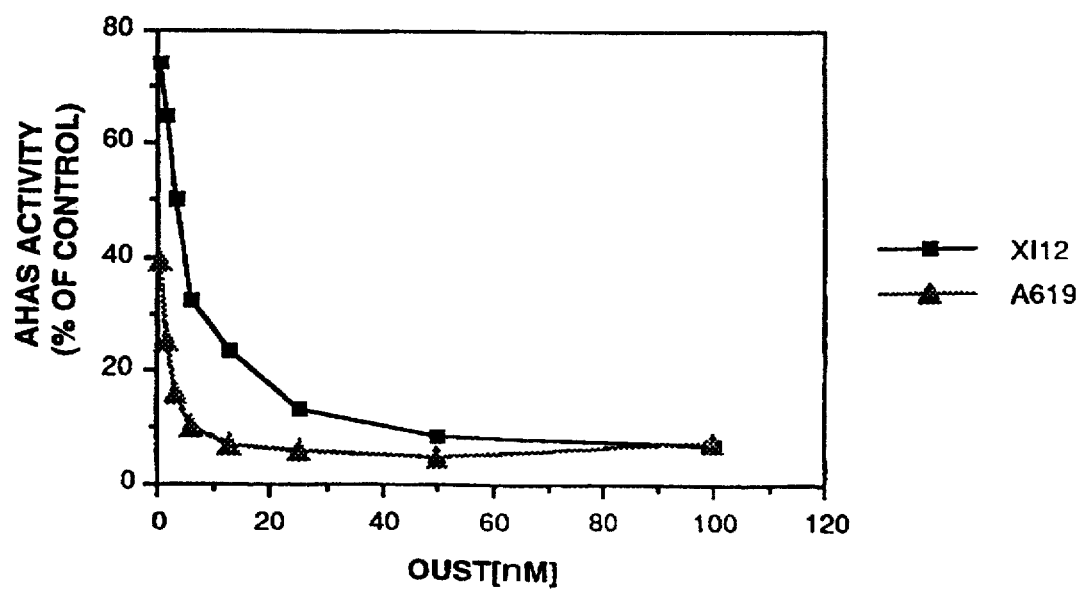

AHAS activity from B73, A619, or other wild-type maize lines is highly sensitive to inhibition by imazethapyr (PURSUIT™) with an I$_{50}$ of 1 uM (See FIG. 1). Contrary to this observation, XI12 shows 70–80% of enzyme activity at the highest concentrations (100 μM) of PURSUIT™ or ARSENAL™ (imazepyr), and about 70% in the presence of SCEPTER™ (imazequin). This result shows a 100-fold increase in tolerance of AHAS activity from XI12 to imazethapyr as compared to the in vitro AHAS activity from A619. Sensitivity of AHAS activity from the two lines to sulfonylureas gives a different picture. In the presence of OUST™ (sulfometuron methyl), at 100 nM, AHAS activity of XI12 is only 15–20%. AHAS activity of A619 in the presence of OUST™ IS 5–10%, and in the presence of PURSUIT™ is 15–20% (See FIG. 1).

3. Cloning of XI12 AHAS Genes

Seeds of the XI12 mutant derived from an imidazolinone resistant corn tissue culture line are planted; plants obtained therefrom appear to be segregating for the mutant AHAS phenotype. In order to obtain homozygous resistant seed material, a population of XI12 mutant plants are selfed. After selecting for herbicide resistance for three consecutive growing seasons, the seeds are homozygous for the mutant AHAS gene. Homozygous seeds are collected and used to grow seedlings to be used in AHAS gene isolation.

DNA is extracted from 7 days old etiolated seedlings of a homozygous XI12 line. 60 g of plant tissue is powdered in liquid nitrogen, and transfered into 108 ml DNA extraction buffer (1.4M NaCl, 2.0% Ctab (hexadecyl trimethyl ammonium bromide), 100 mM tris-Cl pH 8.0, 20 mM EDTA, 2% Mercaptoethanol) and 54 ml water. After incubation at 50°–60° C. for 30 minutes the suspension is extracted with an equal amount of chloroform. The DNA is precipitated by adding an equal amount of precipitation buffer (1% Ctab, 50 mM Tris-Cl pH 8.0, 10 mM EDTA). To purify the genomic DNA, a high speed centrifugation in 6.6M CsCl and ethidium bromide is performed (Ti80 rotor, 50,000 rpm, 20° C., 24 hours). The purified DNA is extracted with salt saturated Butanol and dialyzed for 25 hours against 3 changes of 1 l dialysis buffer (10 mM Tris-Cl Ph 8.0, 1 mM EDTA, 0.1M NaCl). The concentration of the XI12 genomic DNA is determined spectrophotometrically to be 310 mg/ml. The yield is 0.93 mg.

The XI12 genomic DNA is used to create a genomic library in the phage EMBL-3. The DNA is partially digested with MboI and the fragments are separated on a sucrose gradient to produce size range between 8 to 22 kb before cloning into the BamHI site of EMBL-3. After obtaining 2.1×10$^6$ independent clones, the library is amplified once. The titer of the library is determined 9×10$^{10}$ pfu/ml.

To obtain probes for analysis of the XI12 library, a W22 (wild-type) cDNA library in lambda gt11, purchased from Clontech Inc., CA, is screened with an 800 nt BamHI probe isolated from Arabidopsis AHAS genomic clone. The phages are plated in a density of 50,000 pfu/15 cm plate, transferred onto nitrocellulose filters, prehybridized in 6×SSC, 0.2% SDS for 2 hours and hybridized with the Arabidopsis AHAS probe in 6×SSC, 0.2% SDS overnight. One positive phage is identified, further purified and used for subcloning of a 1.1 kb EcoRI fragment. The 1.1 kb EcoRI fragment is subcloned into pGemA-4 and used as a probe to identify the XI12 AHAS genes.

Figure 2A:
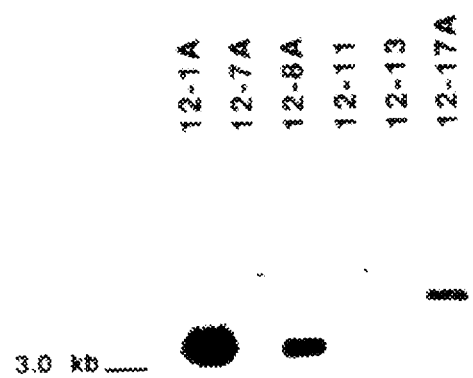
FIGS. 2A and 2B: Southern analysis of genomic clones in phage EMBL3. Phages 12-1A (from W22), 12-7A, 18-8A, 12-11, and 12-17A (From XI12) are digested with XbaI or SalI, separated on a 1% agarose gel, transfered onto nitrocellulose and hybridized with an AHAS cDNA fragment as probe.
Figure 2B:
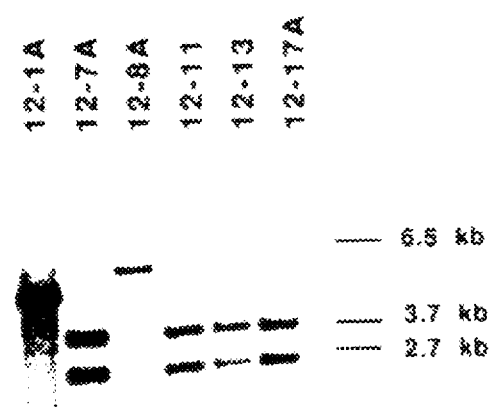
Figure 3:
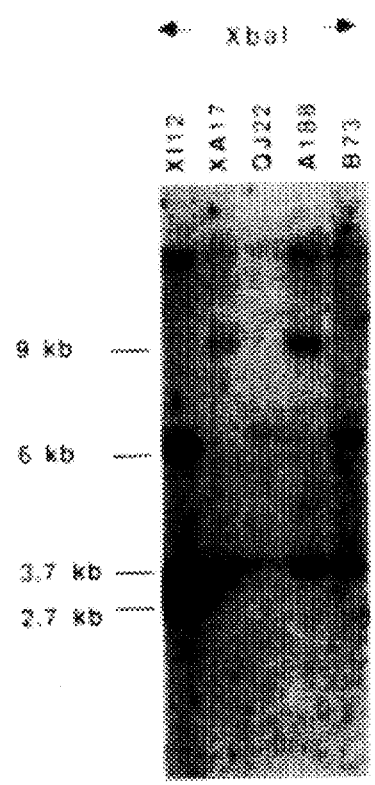
FIG. 3: Southern analysis of genomic DNA from corn lines XI12, XA17, QJ22, A188 and B73. The DNA is digested with XbaI, separated on a 1% agarose gel, transferred onto nitrocellulose and hybridized with an AHAS cDNA fragment as probe.
Figures 4, 5B:
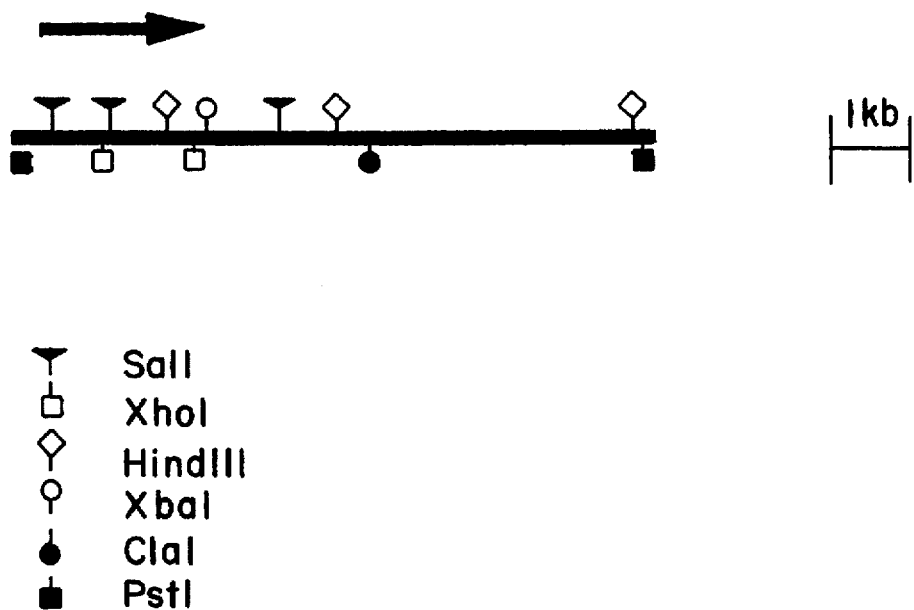
FIG. 4: Restriction map of plasmid pCD8A. The mutant AHAS gene from XI12 was subcloned as a 8 kb PstI fragment into vector pKS(+). The location and orientation of the AHAS gene is indicated by an arrow. The restriction sites of PstI, XhoI, HindIII, XbaI and ClaI are represented by symbols.
FIGS. 5A and 5B: Nucleotide sequencing gel of the non-coding strand (A) and the double stranded DNA sequence (B) of AHAS clones W22/4-4, B73/10-4 and XI12/8A in the region of amino acids 614 to 633. The position of the cytosine to thymidine transition is indicated by an arrow.

The XI12 genomic library is plated on 12 15-cm plates (concentration of 50,000 pfu/plate) and is screened with the W22 AHAS cDNA probe. The filters are prehybridized (2 hours) and hybridized (over night) in Church buffer (0.5M Na Phosphate, 1 mM EDTA, 1% BSA, 7% SDS) at 65° C. and washed at 65° C. in 2×SSC, 0.2% SDS and 0.3×SSC, 0.2% SDS. 12 positive plaques are obtained from a total of $7.5 \times 10^5$ pfu screened and 5 positive clones are further purified and isolated according to Chisholm (BioTechniques 7: 21–23, 1989). Southern analysis (See FIG. 2) showed that the phage clones represented two types of AHAS clones: Type-1 clones contain one large XbaI (>6.5 kb) fragment hybridizing to the AHAS cDNA probe. Type-2 clones contained two 2.7 and 3.7 kb XbaI fragments hybridizing to the AHAS cDNA probe. Genomic Southern of XI12 DNA demonstrated, that the XbaI fragments obtained by digesting genomic DNA and by hybridizing to the AHAS cDNA probe correspond to the XbaI fragments identified in the XI12 phage clones (See FIG. 3). Restriction digest and Southern Analysis also demonstrate that of the 5 AHAS clones, one clone represents the mutant als2 genes and four represent the als1 gene.

The AHAS genes corresponding to the mutant locus located on chromosome 5 (clone 12/8A) and the non-mutant locus located on chromosome 4 (clone 12/17A) are subcloned as a PstI fragment (clone 12/8A) or as XbaI fragment (12/17A) into the sequencing vector pBluescript II KSm13 (+) (pKS+; Stratagene). Both 2.7 kb and 3.7 kb XbaI fragments from phage 12/17A contain one complete copy of AHAS genes which are identified. The sequence of each is obtained by dideoxy sequencing (Pharmacia T7 sequencing Kits) using primers complementary to the AHAS coding sequence.

The methods of DNA extraction, cloning of the genomic library and screening of the library are as described for the XI12 genomic DNA. The B73 AHAS genes are subcloned into the sequencing vector pKS+ as XbaI fragments and are sequenced. The sequence is obtained by dideoxy sequencing, using primers complementary to the AHAS coding sequence as described for the SI12 AHAS genes.

A W22 genomic library in EMBL3 purchased from Clontech Inc., CA is screened. The phages are plated in a density of 50,000 pfu/7 inch plate, transferred onto nitrocellulose filters, and hybridized with the W22 AHAS cDNA probe described above (prehybridization and hybridization conditions: 6×SSC, 0.5% SDS, 1×Denhard's 100 mg/ml calf thymus DNA, 65° C., washing conditions: 3×SSC, 0.2% SDS for 2 hours at 65° C., and 0.3 ×SSC, 0.2% SDS for 2 hours). Two positive phages (12/1A and 12/4-4) are identified and further purified.

The W22 genomic clone 12/1A is subcloned as two 0.78 kb (pGemA-4) and 3.0 kb (pGemA-14; Promega) SalI fragments into the vector pGem-A2, and as a 6.5 kb XbaI fragment into the vector pKS+ (pCD200). The coding strand sequence of the W22 AHAS gene is obtained by dideoxy sequencing of nested deletions created from subclones pGem A-14 and pGem A-4 of phage 12-1A. This sequence is used to design oligonucleotides complementary to the AHAS non-coding strand. The sequence of the non-coding strand is obtained by dideoxy sequencing of clone pCD200 using primers complementary to the coding strand. Upon complementing the sequencing of the W22 AHAS gene, primers of both DNA strands are designed and used for the sequencing of the AHAS genes isolated from the XI12 and B73 genomic libraries.

4. Cloning of QJ22 AHAS Genes

The sequence of the gene encoding AHAS in the maize line QJ22, which is selectively resistant to imidazolinones, is also determined. A genomic library of QJ22 is prepared in an EMBL3 vector. A library of 800,000 phage is screened with an 850 nucleotide SalI/ClaI fragment isolated from an AHAS clone (A-4) derived from the wild-type maize line W22. Five positive phages are picked and submitted to a second round of screening to partially purify the phage. The partially purified phage are analyzed by PCR to determine if any clones represent the QJ22 als1 gene. Such clones are identified as a 3.7kb XbaI fragment with a gene specific SmaI site at position 495. The second screen indicates the presence of a single positive clone with these characteristics.

The PCR product is purified using a commercial kit (Magic PCR Preps) from Promega, and the purified DNA is sequenced with a Taq polymerase sequencing system "fmol", also from Promega Sequence analysis of both strands of the DNA of the QJ22 mutant AHAS shows a nucleotide transition from G to A in the codon for amino acid 621. This mutation is identical to the one seen in XI12 and the remainder of the sequence is typical of an als1 gene.

RESULTS

The sequence of the mutant AHAS genes is compared with the sequences obtained from the wild type corn lines B73 and W22 (See FIG. 7). The XI12 mutant gene (XI12/8A) and the wild type gene are identical except for the amino acid change at position 621, causing a single nucleotide transition from AGT to AAT (See FIG. 8). The XI12 mutant XI12/8A and the wild-type B73/7-4 gene show an additional difference at position 63. On the other hand, the non-mutant XI12 AHAS gene cloned in XI12/17A is completely homologous to the corresponding B73/10-2 in the region coding for the mature AHAS protein (data not shown). The QJ22 mutant gene is identical to the non-mutant XI12 AHAS gene except for the amino acid changed position 621.

DEPOSIT OF BIOLOGICAL MATERIALS

The following biological materials were deposited with the American Type Culture Collection, 12301 Parklawn Drive, Rockville, Md., 20857, as follows:

E. coli XLI Blue harboring plasmid pX12/8A, deposited on Jul. 3, 1991, Accession Number ATCC 68643

XI12 corn seed deposited on Jul. 16, 1991, Accession Number ATCC 75051.

What we claim is:

1. A mature plant resistant to imidazolinones but not to sulfonylureas which plant has acquired a maize nucleic acid sequence encoding a functional AHAS enzyme, which enzyme has an amino acid substitution for serine at position 621 relative to a wild-type maize AHAS enzyme wherein said substitution is from Ser to Asn in the conserved C-terminal region and which substitution confers imidazolinone-specific resistance to the enzyme, by transformation with the sequence or by inheritance with a plant transformed with the sequence.

2. A seed of the plant of claim 1.

3. Pollen of the plant of claim 1.

4. A method for growing plants resistant to imidazolinones but not to sulfonylureas which comprises cultivating the plant of claim 1, in the presence of a herbicidal amount of at least one imidazolinone.

5. The mature plant of claim 1 wherein the substitution at serine is to asparagine at position 621.

6. The seed of claim 2 where n the substitution at serine is to asparagine at position 621.

7. Pollen according to claim 3 wherein the substitution at serine is to asparagine at position 621.

8. A viable seed derived from the plant of claim 1.

9. A viable seed derived from the seed of claim 2.

10. A viable seed derived from a plant developed from the pollen of claim 3.

11. The plant of claim 1 wherein said plant is a monocot.

12. The seed of claim 2 wherein said seed is a monocot.

13. The pollen of claim 3 wherein said pollen is a monocot.

14. The plant of claim 1 wherein said plant is maize.

15. The seed of claim 2 wherein said seed is maize.

16. The pollen of claim 3 wherein said pollen is a maize.

17. The mature plant of claim 14 wherein the substitution at serine is to asparagine at position 621.

18. The seed of claim 15 wherein the substitution at serine is to asparagine at position 621.

19. Pollen according to claim 16 wherein the substitution at serine is to asparagine at position 621.

20. A method for growing plants resistant to imidazolinones but not to sulfonylureas, which comprises cultivating the seed of claim 2 in the presence of a herbicidal amount of at least one imidazolinone.

21. The method of claim 4 wherein said plant that is cultivated has the substitution of asparagine for serine at position 621.

22. The method of claim 20 wherein said seed that is cultivated has the substitution of asparagine for serine at position 621.

23. A method for growing plants resistant to imidazolinones but not to sulfonylureas, which comprises cultivating the seed of claim 9 in the presence of a herbicidal amount of at least one imidazolinone.

24. A method for growing plants resistant to imidazolinones but not to sulfonylureas, which comprises cultivating the seed of claim 10 in the presence of a herbicidal amount of at least one imidazolinone.

25. A method for growing plants resistant to imidazolinones but not to sulfonylureas, which comprises cultivating the plant of claim 11 in the presence of a herbicidal amount of at least one imidazolinone.

26. The method of claim 4 wherein said plant is a monocot.

27. The method of claim 20 wherein said seed is a monocot.

28. The method of claim 26 wherein said plant is maize.

29. The method of claim 27 wherein said seed is maize.

30. The method of claim 28 wherein said plant that is cultivated has the substitution of asparagine for serine at position 621.

31. A viable seed derived from the plant of claim 14.

32. A viable seed derived from the seed of claim 15.

33. A viable seed derived from the plant of claim 17.

34. A viable seed derived from the seed of claim 18.

35. A method for growing plants resistant to imidazolinones but not to sulfonylureas, which comprises cultivating the seed of claim 31 in the presence of a herbicidal amount of at least one imidazolinone.

36. A method for growing plants resistant to imidazolinones but not to sulfonylureas, which comprises cultivating the seed of claim 32 in the presence of a herbicidal amount of at least one imidazolinone.

37. A method for growing plants resistant to imidazolinones but not to sulfonylureas, which comprises cultivating the seed of claim 33 in the presence of a herbicidal amount of at least one imidazolinone.

38. A method for growing plants resistant to imidazolinones but not to sulfonylureas, which comprises cultivating the seed of claim 34 in the presence of a herbicidal amount of at least one imidazolinone.

39. A plant of claim 11 wherein the substitution at serine is to asparagine at position 621.

40. A seed of claim 12 wherein the substitution at serine is to asparagine at position 621.

41. The method of claim 29 wherein said seed that is cultivated has the substitution of asparagine for serine at position 621.

\* \* \* \* \*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 1969 BP's and 638 Amino Acids
( B ) TYPE: Nucleotide and Amino Acid
( C ) STRANDEDNESS: Single
( E ) TOPOLOGY: Linear ( i i ) MOLECULE TYPE: DNA and Protein ( x i ) SEQUENCE DESCRIPTION: SEQ ID NO: 1:

```
AACCCTCGCG  CCGCCTCCGA  GACAGCCGCC  GCAACC                                          36

ATG  GCC  ACC  GCC  GCC  GCC  GCG  TCT  ACC  GCG  CTC  ACT                          72
Met  Ala  Thr  Ala  Ala  Ala  Ala  Ser  Thr  Ala  Leu  Thr
 1                  5                       10

GGC  GCC  ACT  ACC  GCT  GCG  CCC  AAG  GCG  AGG  CGC  CGG                         108
Gly  Ala  Thr  Thr  Ala  Ala  Pro  Lys  Ala  Arg  Arg  Arg
               15                      20

GCG  CAC  CTC  CTG  GCC  ACC  CGC  CGC  GCC  CTC  GCC  GCG                         144
Ala  His  Leu  Leu  Ala  Thr  Arg  Arg  Ala  Leu  Ala  Ala
 25                      30                      35

CCC  ATC  AGG  TGC  TCA  GCG  GCG  TCA  CCC  GCC  ATG  CCG                         180
Pro  Ile  Arg  Cys  Ser  Ala  Ala  Ser  Pro  Ala  Met  Pro
                40                       45

ATG  GCT  CCC  CCG  GCC  ACC  CCG  CTC  CGG  CCG  TGG  GGC                         216
Met  Ala  Pro  Pro  Ala  Thr  Pro  Leu  Arg  Pro  Trp  Gly
      50                       55                      60

CCC  ACC  GAT  CCC  CGC  AAG  GGC  GCC  GAC  ATC  CTC  GTC                         252
Pro  Thr  Asp  Pro  Arg  Lys  Gly  Ala  Asp  Ile  Leu  Val
                     65                      70

GAG  TCC  CTC  GAG  CGC  TGC  GGC  GTC  CGC  GAC  GTC  TTC                         288
Glu  Ser  Leu  Glu  Arg  Cys  Gly  Val  Arg  Asp  Val  Phe
           75                      80

GCC  TAC  CCC  GGC  GGC  GCG  TCC  ATG  GAG  ATC  CAC  CAG                         324
Ala  Tyr  Pro  Gly  Gly  Ala  Ser  Met  Glu  Ile  His  Gln
 85                      90                      95

GCA  CTC  ACC  CGC  TCC  CCC  GTC  ATC  GCC  AAC  CAC  CTC                         360
Ala  Leu  Thr  Arg  Ser  Pro  Val  Ile  Ala  Asn  His  Leu
               100                     105

TTC  CGC  CAC  GAG  CAA  GGG  GAG  GCC  TTT  GCG  GCC  TCC                         396
Phe  Arg  His  Glu  Gln  Gly  Glu  Ala  Phe  Ala  Ala  Ser
      110                     115                     120

GGC  TAC  GCG  CGC  TCC  TCG  GGC  CGC  GTC  GGC  GTC  TGC                         432
Gly  Tyr  Ala  Arg  Ser  Ser  Gly  Arg  Val  Gly  Val  Cys
                125                     130

ATC  GCC  ACC  TCC  GGC  CCC  GGC  GCC  ACC  AAC  CTT  GTC                         468
Ile  Ala  Thr  Ser  Gly  Pro  Gly  Ala  Thr  Asn  Leu  Val
                135                     140

TCC  GCG  CTC  GCC  GAC  GCG  CTG  CTC  GAT  TCC  GTC  CCC                         504
Ser  Ala  Leu  Ala  Asp  Ala  Leu  Leu  Asp  Ser  Val  Pro
145                     150                     155

ATG  GTC  GCC  ATC  ACG  GGA  CAG  GTG  CCG  CGA  CGC  ATG                         540
Met  Val  Ala  Ile  Thr  Gly  Gln  Val  Pro  Arg  Arg  Met
                160                     165

ATT  GGC  ACC  GAC  GCC  TTC  CAG  GAG  ACG  CCC  ATC  GTC                         576
Ile  Gly  Thr  Asp  Ala  Phe  Gln  Glu  Thr  Pro  Ile  Val
```

-continued

|  |  |  |  | 170 |  |  |  | 175 |  |  |  | 180 |  |  |
|---|---|---|---|---|---|---|---|---|---|---|---|---|---|---|
| GAG | GTC | ACC | CGC | TCC | ATC | ACC | AAG | CAC | AAC | TAC | CTG | | | 612 |
| Glu | Val | Thr | Arg | Ser | Ile | Thr | Lys | His | Asn | Tyr | Leu | | | |
|  |  |  |  | 185 |  |  |  | 190 |  |  |  | | | |

| GTC | CTC | GAC | GTC | GAC | GAC | ATC | CCC | CGC | GTC | GTG | CAG | 648 |
| Val | Leu | Asp | Val | Asp | Asp | Ile | Pro | Arg | Val | Val | Gln | |
|  |  |  | 195 |  |  |  |  | 200 |  |  |  | |

| GAG | GCT | TTC | TTC | CTC | GCC | TCC | TCT | GGT | CGA | CCG | GGG | 684 |
| Glu | Ala | Phe | Phe | Leu | Ala | Ser | Ser | Gly | Arg | Pro | Gly | |
| 205 |  |  |  |  | 210 |  |  |  |  | 215 |  | |

| CCG | GTG | CTT | GTC | GAC | ATC | CCC | AAG | GAC | ATC | CAG | CAG | 720 |
| Pro | Val | Leu | Val | Asp | Ile | Pro | Lys | Asp | Ile | Gln | Gln | |
|  |  |  | 220 |  |  |  | 225 |  |  |  |  | |

| CAG | ATG | GCG | GTG | CCT | GTC | TGG | GAC | AAG | CCC | ATG | AGT | 756 |
| Gln | Met | Ala | Val | Pro | Val | Trp | Asp | Lys | Pro | Met | Ser | |
|  | 230 |  |  |  |  | 235 |  |  |  |  | 240 | |

| CTG | CCT | GGG | TAC | ATT | GCG | CGC | CTT | CCC | AAG | CCC | CCT | 792 |
| Leu | Pro | Gly | Tyr | Ile | Ala | Arg | Leu | Pro | Lys | Pro | Pro | |
|  |  |  |  | 245 |  |  |  |  | 250 |  |  | |

| GCG | ACT | GAG | TTG | CTT | GAG | CAG | GTG | CTG | CGT | CTT | GTT | 828 |
| Ala | Thr | Glu | Leu | Leu | Glu | Gln | Val | Leu | Arg | Leu | Val | |
|  |  | 255 |  |  |  |  | 260 |  |  |  |  | |

| GGT | GAA | TCC | CGG | CGC | CCT | GTT | CTT | TAT | GTT | GGC | GGT | 864 |
| Gly | Glu | Ser | Arg | Arg | Pro | Val | Leu | Tyr | Val | Gly | Gly | |
| 265 |  |  |  |  | 270 |  |  |  |  | 275 |  | |

| GCG | TGC | GCA | GCA | TCT | GGT | GAG | GAG | TTG | CGA | CGC | TTT | 900 |
| Ala | Cys | Ala | Ala | Ser | Gly | Glu | Glu | Leu | Arg | Arg | Phe | |
|  |  |  | 280 |  |  |  |  | 285 |  |  |  | |

| GTG | GAG | CTG | ACT | GGA | ATC | CCG | GTC | ACA | ACT | ACT | CTT | 936 |
| Val | Glu | Leu | Thr | Gly | Ile | Pro | Val | Thr | Thr | Thr | Leu | |
|  | 290 |  |  |  |  | 295 |  |  |  |  | 300 | |

| ATG | GGC | CTC | GGC | AAC | TTC | CCC | AGC | GAC | GAC | CCA | CTG | 972 |
| Met | Gly | Leu | Gly | Asn | Phe | Pro | Ser | Asp | Asp | Pro | Leu | |
|  |  |  |  | 305 |  |  |  |  | 310 |  |  | |

| TCT | CTG | CGC | ATG | CTA | GGT | ATG | CAT | GGC | ACG | GTG | TAT | 1008 |
| Ser | Leu | Arg | Met | Leu | Gly | Met | His | Gly | Thr | Val | Tyr | |
|  |  | 315 |  |  |  |  | 320 |  |  |  |  | |

| GCA | AAT | TAT | GCA | GTG | GAT | AAG | GCC | GAT | CTG | TTG | CTT | 1044 |
| Ala | Asn | Tyr | Ala | Val | Asp | Lys | Ala | Asp | Leu | Leu | Leu | |
| 325 |  |  |  |  | 330 |  |  |  |  | 335 |  | |

| GCA | CTT | GGT | GTG | CGG | TTT | GAT | GAT | CGT | GTG | ACA | GGG | 1080 |
| Ala | Leu | Gly | Val | Arg | Phe | Asp | Asp | Arg | Val | Thr | Gly | |
|  |  |  | 340 |  |  |  |  | 345 |  |  |  | |

| AAG | ATT | GAG | GCT | TTT | GCA | AGC | AGG | GCT | AAG | ATT | GTG | 1116 |
| Lys | Ile | Glu | Ala | Phe | Ala | Ser | Arg | Ala | Lys | Ile | Val | |
|  |  | 350 |  |  |  |  | 355 |  |  |  | 360 | |

| CAC | GTT | GAT | ATT | GAT | CCG | GCT | GAG | ATT | GGC | AAG | AAC | 1152 |
| His | Val | Asp | Ile | Asp | Pro | Ala | Glu | Ile | Gly | Lys | Asn | |
|  |  |  |  | 365 |  |  |  |  | 370 |  |  | |

| AAG | CAG | CCA | CAT | GTG | TCC | ATC | TGT | GCA | GAT | GTT | AAG | 1188 |
| Lys | Gln | Pro | His | Val | Ser | Ile | Cys | Ala | Asp | Val | Lys | |
|  |  | 375 |  |  |  |  | 380 |  |  |  |  | |

| CTT | GCT | TTG | CAG | GGC | ATG | AAT | GCT | CTT | CTT | GAA | GGA | 1224 |
| Leu | Ala | Leu | Gln | Gly | Met | Asn | Ala | Leu | Leu | Glu | Gly | |
| 385 |  |  |  |  | 390 |  |  |  |  | 395 |  | |

| AGC | ACA | TCA | AAG | AAG | AGC | TTT | GAC | TTT | GGC | TCA | TGG | 1260 |
| Ser | Thr | Ser | Lys | Lys | Ser | Phe | Asp | Phe | Gly | Ser | Trp | |
|  |  |  | 400 |  |  |  |  | 405 |  |  |  | |

| AAC | GAT | GAG | TTG | GAT | CAG | CAG | AAG | AGG | GAA | TTC | CCC | 1296 |
| Asn | Asp | Glu | Leu | Asp | Gln | Gln | Lys | Arg | Glu | Phe | Pro | |

-continued

|  |  |  |  |  |  |  |  |  |  |  |  |
|---|---|---|---|---|---|---|---|---|---|---|---|
| | | 410 | | | | 415 | | | | 420 | |
| CTT | GGG | TAT | AAA | ACA | TCT | AAT | GAG | GAG | ATC | CAG | CCA |
| Leu | Gly | Tyr | Lys | Thr | Ser | Asn | Glu | Glu | Ile | Gln | Pro |
| | | | 425 | | | | | 430 | | | | 1332

| CAA | TAT | GCT | ATT | CAG | GTT | CTT | GAT | GAG | CTG | ACG | AAA |
| Gln | Tyr | Ala | Ile | Gln | Val | Leu | Asp | Glu | Leu | Thr | Lys |
| | | 435 | | | | 440 | | | | | | 1368

| GGC | GAG | GCC | ATC | ATC | GGC | ACA | GGT | GTT | GGG | CAG | CAC |
| Gly | Glu | Ala | Ile | Ile | Gly | Thr | Gly | Val | Gly | Gln | His |
| 445 | | | | 450 | | | | | 455 | | | 1404

| CAT | ATG | TGG | GCG | GCA | CAG | TAC | TAC | ACT | TAC | AAG | CGG |
| Gln | Met | Trp | Ala | Ala | Gln | Tyr | Tyr | Thr | Tyr | Lys | Arg |
| | | | 460 | | | | 465 | | | | | 1440

| CCA | AGG | CAG | TGG | TTG | TCT | TCA | GCT | GGT | CTT | GGG | GCT |
| Pro | Arg | Gln | Trp | Leu | Ser | Ser | Ala | Gly | Leu | Gly | Ala |
| | 470 | | | | 475 | | | | 480 | | | 1476

| ATG | GGA | TTT | GGT | TTG | CCG | GCT | GCT | GCT | GGT | GCT | TCT |
| Met | Gly | Phe | Gly | Leu | Pro | Ala | Ala | Ala | Gly | Ala | Ser |
| | | | 485 | | | | | 490 | | | | 1512

| GTG | GCC | AAC | CCA | GGT | GTT | ACT | GTT | GTT | GAC | ATC | GAT |
| Val | Ala | Asn | Pro | Gly | Val | Thr | Val | Val | Asp | Ile | Asp |
| | | 495 | | | | 500 | | | | | | 1548

| GGA | GAT | GGT | AGC | TTT | CTC | ATG | AAC | GTT | CAG | GAG | CTA |
| Gly | Asp | Gly | Ser | Phe | Leu | Met | Asn | Val | Gln | Glu | Leu |
| 505 | | | | 510 | | | | 515 | | | | 1584

| GCT | ATG | ATC | CGA | ATT | GAG | AAC | CTC | CCG | GTG | AAG | GTC |
| Ala | Met | Ile | Arg | Ile | Glu | Asn | Leu | Pro | Val | Lys | Val |
| | | | 520 | | | | 525 | | | | | 1620

| TTT | GTG | CTA | AAC | AAC | CAG | CAC | CTG | GGG | ATG | GTG | GTG |
| Phe | Val | Leu | Asn | Asn | Gln | His | Leu | Gly | Met | Val | Val |
| | 530 | | | | 535 | | | | 540 | | | 1656

| CAG | TGG | GAG | GAC | AGG | TTC | TAT | AAG | GCC | AAC | AGA | GCG |
| Gln | Trp | Glu | Asp | Arg | Phe | Tyr | Lys | Ala | Asn | Arg | Ala |
| | | | 545 | | | | 550 | | | | | 1692

| CAC | ACA | TAC | TTG | GGA | AAC | CCA | GAG | AAT | GAA | AGT | GAG |
| His | Thr | Tyr | Leu | Gly | Asn | Pro | Glu | Asn | Glu | Ser | Glu |
| | | 555 | | | | 560 | | | | | | 1728

| ATA | TAT | CCA | GAT | TTC | GTG | ACG | ATC | GCC | AAA | GGG | TTC |
| Ile | Tyr | Pro | Asp | Phe | Val | Thr | Ile | Ala | Lys | Gly | Phe |
| 565 | | | | 570 | | | | | 575 | | | 1764

| AAC | ATT | CCA | GCG | GTC | CGT | GTG | ACA | AAG | AAG | AAC | GAA |
| Asn | Ile | Pro | Ala | Val | Arg | Val | Thr | Lys | Lys | Asn | Glu |
| | | | 580 | | | | 585 | | | | | 1800

| GTC | CGC | GCA | GCG | ATA | AAG | AAG | ATG | CTC | GAG | ACT | CCA |
| Val | Arg | Ala | Ala | Ile | Lys | Lys | Met | Leu | Glu | Thr | Pro |
| | 590 | | | | 595 | | | | 600 | | | 1836

| GGG | CCG | TAC | CTC | TTG | GAT | ATA | ATC | GTC | CCA | CAC | CAG |
| Gly | Pro | Tyr | Leu | Leu | Asp | Ile | Ile | Val | Pro | His | Gln |
| | | | 605 | | | | 610 | | | | | 1872

| GAG | CAT | GTG | TTG | CCT | ATG | ATC | CCT | AAT | GGT | GGG | GCT |
| Glu | His | Val | Leu | Pro | Met | Ile | Pro | Asn | Gly | Gly | Ala |
| | | 615 | | | | 620 | | | | | | 1908

| TTC | AAG | GAT | ATG | ATC | CTG | GAT | GGT | GAT | GGC | AGG | ACT |
| Phe | Lys | Asp | Met | Ile | Leu | Asp | Gly | Asp | Gly | Arg | Thr |
| 625 | | | | 630 | | | | | 635 | | | 1944

| GTG | TAC |
| Val | Tyr |
| 638 | | 1950

TGATCTAAAA TCCAGCAAG          1969

( 2 ) INFORMATION FOR SEQ ID NO: 2:

( i ) SEQUENCE CHARACTERISTICS:
        ( A ) LENGTH: 1969 BP's and 638 Amino Acids
        ( B ) TYPE: Nucleotide and Amino Acid
        ( C ) STRANDEDNESS: Single
        ( E ) TOPOLOGY: Linear ( i i ) MOLECULE TYPE: DNA and Protein ( x i ) SEQUENCE DESCRIPTION: SEQ ID NO: 2:

```
AACCCTCGCG CCGCCTCCGA GACAGCCGCC GCAACC                                    36

ATG GCC ACC GCC GCC GCC GCG TCT ACC GCG CTC ACT                            72
Met Ala Thr Ala Ala Ala Ala Ser Thr Ala Leu Thr
 1               5                  10

GGC GCC ACT ACC GCT GCG CCC AAG GCG AGG CGC CGG                           108
Gly Ala Thr Thr Ala Ala Pro Lys Ala Arg Arg Arg
         15                  20

GCG CAC CTC CTG GCC ACC CGC CGC GCC CTC GCC GCG                           144
Ala His Leu Leu Ala Thr Arg Arg Ala Leu Ala Ala
 25                  30                  35

CCC ATC AGG TGC TCA GCG GCG TCA CCC GCC ATG CCG                           180
Pro Ile Arg Cys Ser Ala Ala Ser Pro Ala Met Pro
             40                  45

ATG GCT CCC CCG GCC ACC CCG CTC CGG CCG TGG GGC                           216
Met Ala Pro Pro Ala Thr Pro Leu Arg Pro Trp Gly
 50                  55                  60

CCC ACC GAT CCC CGC AAG GGC GCC GAC ATC CTC GTC                           252
Pro Thr Asp Pro Arg Lys Gly Ala Asp Ile Leu Val
                 65                  70

GAG TCC CTC GAG CGC TGC GGC GTC CGC GAC GTC TTC                           288
Glu Ser Leu Glu Arg Cys Gly Val Arg Asp Val Phe
         75                  80

GCC TAC CCC GGC GGC GCG TCC ATG GAG ATC CAC CAG                           324
Ala Tyr Pro Gly Gly Ala Ser Met Glu Ile His Gln
 85                  90                  95

GCA CTC ACC CGC TCC CCC GTC ATC GCC AAC CAC CTC                           360
Ala Leu Thr Arg Ser Pro Val Ile Ala Asn His Leu
             100                 105

TTC CGC CAC GAG CAA GGG GAG GCC TTT GCG GCC TCC                           396
Phe Arg His Glu Gln Gly Glu Ala Phe Ala Ala Ser
     110                 115                 120

GGC TAC GCG CGC TCC TCG GGC CGC GTC GGC GTC TGC                           432
Gly Tyr Ala Arg Ser Ser Gly Arg Val Gly Val Cys
                 125                 130

ATC GCC ACC TCC GGC CCC GGC GCC ACC AAC CTT GTC                           468
Ile Ala Thr Ser Gly Pro Gly Ala Thr Asn Leu Val
         135                 140

TCC GCG CTC GCC GAC GCG CTG CTC GAT TCC GTC CCC                           504
Ser Ala Leu Ala Asp Ala Leu Leu Asp Ser Val Pro
145                 150                 155

ATG GTC GCC ATC ACG GGA CAG GTG CCG CGA CGC ATG                           540
Met Val Ala Ile Thr Gly Gln Val Pro Arg Arg Met
             160                 165

ATT GGC ACC GAC GCC TTC CAG GAG ACG CCC ATC GTC                           576
Ile Gly Thr Asp Ala Phe Gln Glu Thr Pro Ile Val
     170                 175                 180

GAG GTC ACC CGC TCC ATC ACC AAG CAC AAC TAC CTG                           612
Glu Val Thr Arg Ser Ile Thr Lys His Asn Tyr Leu
                 185                 190

GTC CTC GAC GTC GAC GAC ATC CCC CGC GTC GTG CAG                           648
```

-continued

```
                Val Leu Asp Val Asp Asp Ile Pro Arg Val Val Gln
                        195             200

GAG GCT TTC TTC CTC GCC TCC TCT GGT CGA CCG GGG                    684
Glu Ala Phe Phe Leu Ala Ser Ser Gly Arg Pro Gly
205                 210                 215

CCG GTG CTT GTC GAC ATC CCC AAG GAC ATC CAG CAG                    720
Pro Val Leu Val Asp Ile Pro Lys Asp Ile Gln Gln
                    220                 225

CAG ATG GCG GTG CCT GTC TGG GAC AAG CCC ATG AGT                    756
Gln Met Ala Val Pro Val Trp Asp Lys Pro Met Ser
    230                 235                 240

CTG CCT GGG TAC ATT GCG CGC CTT CCC AAG CCC CCT                    792
Leu Pro Gly Tyr Ile Ala Arg Leu Pro Lys Pro Pro
                245                 250

GCG ACT GAG TTG CTT GAG CAG GTG CTG CGT CTT GTT                    828
Ala Thr Glu Leu Leu Glu Gln Val Leu Arg Leu Val
        255                 260

GGT GAA TCC CGG CGC CCT GTT CTT TAT GTT GGC GGT                    864
Gly Glu Ser Arg Arg Pro Val Leu Tyr Val Gly Gly
265                 270                 275

GCG TGC GCA GCA TCT GGT GAG GAG TTG CGA CGC TTT                    900
Ala Cys Ala Ala Ser Gly Glu Glu Leu Arg Arg Phe
            280                 285

GTG GAG CTG ACT GGA ATC CCG GTC ACA ACT ACT CTT                    936
Val Glu Leu Thr Gly Ile Pro Val Thr Thr Thr Leu
    290                 295                 300

ATG GGC CTC GGC AAC TTC CCC AGC GAC GAC CCA CTG                    972
Met Gly Leu Gly Asn Phe Pro Ser Asp Asp Pro Leu
                305                 310

TCT CTG CGC ATG CTA GGT ATG CAT GGC ACG GTG TAT                   1008
Ser Leu Arg Met Leu Gly Met His Gly Thr Val Tyr
        315                 320

GCA AAT TAT GCA GTG GAT AAG GCC GAT CTG TTG CTT                   1044
Ala Asn Tyr Ala Val Asp Lys Ala Asp Leu Leu Leu
325                 330                 335

GCA CTT GGT GTG CGG TTT GAT GAT CGT GTG ACA GGG                   1080
Ala Leu Gly Val Arg Phe Asp Asp Arg Val Thr Gly
            340                 345

AAG ATT GAG GCT TTT GCA AGC AGG GCT AAG ATT GTG                   1116
Lys Ile Glu Ala Phe Ala Ser Arg Ala Lys Ile Val
    350                 355                 360

CAC GTT GAT ATT GAT CCG GCT GAG ATT GGC AAG AAC                   1152
His Val Asp Ile Asp Pro Ala Glu Ile Gly Lys Asn
                365                 370

AAG CAG CCA CAT GTG TCC ATC TGT GCA GAT GTT AAG                   1188
Lys Gln Pro His Val Ser Ile Cys Ala Asp Val Lys
        375                 380

CTT GCT TTG CAG GGC ATG AAT GCT CTT CTT GAA GGA                   1224
Leu Ala Leu Gln Gly Met Asn Ala Leu Leu Glu Gly
385                 390                 395

AGC ACA TCA AAG AAG AGC TTT GAC TTT GGC TCA TGG                   1260
Ser Thr Ser Lys Lys Ser Phe Asp Phe Gly Ser Trp
            400                 405

AAC GAT GAG TTG GAT CAG CAG AAG AGG GAA TTC CCC                   1296
Asn Asp Glu Leu Asp Gln Gln Lys Arg Glu Phe Pro
    410                 415                 420

CTT GGG TAT AAA ACA TCT AAT GAG GAG ATC CAG CCA                   1332
Leu Gly Tyr Lys Thr Ser Asn Glu Glu Ile Gln Pro
                425                 430

CAA TAT GCT ATT CAG GTT CTT GAT GAG CTG ACG AAA                   1368
```

```
            Gln Tyr Ala Ile Gln Val Leu Asp Glu Leu Thr Lys
                    435             440

GGC GAG GCC ATC ATC GGC ACA GGT GTT GGG CAG CAC                      1404
Gly Glu Ala Ile Ile Gly Thr Gly Val Gly Gln His
445             450                 455

CAT ATG TGG GCG GCA CAG TAC TAC ACT TAC AAG CGG                      1440
Gln Met Trp Ala Ala Gln Tyr Tyr Thr Tyr Lys Arg
            460             465

CCA AGG CAG TGG TTG TCT TCA GCT GGT CTT GGG GCT                      1476
Pro Arg Gln Trp Leu Ser Ser Ala Gly Leu Gly Ala
    470             475             480

ATG GGA TTT GGT TTG CCG GCT GCT GCT GGT GCT TCT                      1512
Met Gly Phe Gly Leu Pro Ala Ala Ala Gly Ala Ser
                485             490

GTG GCC AAC CCA GGT GTT ACT GTT GTT GAC ATC GAT                      1548
Val Ala Asn Pro Gly Val Thr Val Val Asp Ile Asp
            495             500

GGA GAT GGT AGC TTT CTC ATG AAC GTT CAG GAG CTA                      1584
Gly Asp Gly Ser Phe Leu Met Asn Val Gln Glu Leu
505             510             515

GCT ATG ATC CGA ATT GAG AAC CTC CCG GTG AAG GTC                      1620
Ala Met Ile Arg Ile Glu Asn Leu Pro Val Lys Val
            520             525

TTT GTG CTA AAC AAC CAG CAC CTG GGG ATG GTG GTG                      1656
Phe Val Leu Asn Asn Gln His Leu Gly Met Val Val
    530             535             540

CAG TGG GAG GAC AGG TTC TAT AAG GCC AAC AGA GCG                      1692
Gln Trp Glu Asp Arg Phe Tyr Lys Ala Asn Arg Ala
                545             550

CAC ACA TAC TTG GGA AAC CCA GAG AAT GAA AGT GAG                      1728
His Thr Tyr Leu Gly Asn Pro Glu Asn Glu Ser Glu
            555             560

ATA TAT CCA GAT TTC GTG ACG ATC GCC AAA GGG TTC                      1764
Ile Tyr Pro Asp Phe Val Thr Ile Ala Lys Gly Phe
565             570             575

AAC ATT CCA GCG GTC CGT GTG ACA AAG AAG AAC GAA                      1800
Asn Ile Pro Ala Val Arg Val Thr Lys Lys Asn Glu
            580             585

GTC CGC GCA GCG ATA AAG AAG ATG CTC GAG ACT CCA                      1836
Val Arg Ala Ala Ile Lys Lys Met Leu Glu Thr Pro
    590             595             600

GGG CCG TAC CTC TTG GAT ATA ATC GTC CCA CAC CAG                      1872
Gly Pro Tyr Leu Leu Asp Ile Ile Val Pro His Gln
                605             610

GAG CAT GTG TTG CCT ATG ATC CCT AGT GGT GGG GCT                      1908
Glu His Val Leu Pro Met Ile Pro Ser Gly Gly Ala
            615             620

TTC AAG GAT ATG ATC CTG GAT GGT GAT GGC AGG ACT                      1944
Phe Lys Asp Met Ile Leu Asp Gly Asp Gly Arg Thr
625             630             635

GTG TAC                                                              1950
Val Tyr
    638

TGATCTAAAA TCCAGCAAG                                                 1969
```

( 2 ) INFORMATION FOR SEQ ID NO: 3:

( i ) SEQUENCE CHARACTERISTICS:
        ( A ) LENGTH: 1969 BP's and 638 Amino Acids
        ( B ) TYPE: Nucleotide and Amino Acid
        ( C ) STRANDEDNESS: Single ( E ) TOPOLOGY: Linear ( i i ) MOLECULE TYPE: DNA and Protein ( x i ) SEQUENCE DESCRIPTION: SEQ ID NO: 3:

```
AACCCTCGCG CCGCCTCCGA GACAGCCGCC GCAACC                                              36

ATG  GCC  ACC  GCC  GCC  GCC  GCG  TCT  ACC  GCG  CTC  ACT                          72
Met  Ala  Thr  Ala  Ala  Ala  Ala  Ser  Thr  Ala  Leu  Thr
 1              5                             10

GGC  GCC  ACT  ACC  GCT  GCG  CCC  AAG  GCG  AGG  CGC  CGG                         108
Gly  Ala  Thr  Thr  Ala  Ala  Pro  Lys  Ala  Arg  Arg  Arg
          15                       20

GCG  CAC  CTC  CTG  GCC  ACC  CGC  CGC  GCC  CTC  GCC  GCG                         144
Ala  His  Leu  Leu  Ala  Thr  Arg  Arg  Ala  Leu  Ala  Ala
 25                      30                           35

CCC  ATC  AGG  TGC  TCA  GCG  GCG  TCA  CCC  GCC  ATG  CCG                         180
Pro  Ile  Arg  Cys  Ser  Ala  Ala  Ser  Pro  Ala  Met  Pro
               40                       45

ATG  GCT  CCC  CCG  GCC  ACC  CCG  CTC  CGG  CCG  TGG  GGC                         216
Met  Ala  Pro  Pro  Ala  Thr  Pro  Leu  Arg  Pro  Trp  Gly
 50                      55                           60

CCC  ACC  GAG  CCC  CGC  AAG  GGT  GCT  GAC  ATC  CTC  GTC                         252
Pro  Thr  Glu  Pro  Arg  Lys  Gly  Ala  Asp  Ile  Leu  Val
                    65                       70

GAG  TCC  CTC  GAG  CGC  TGC  GGC  GTC  CGC  GAC  GTC  TTC                         288
Glu  Ser  Leu  Glu  Arg  Cys  Gly  Val  Arg  Asp  Val  Phe
               75                       80

GCC  TAC  CCC  GGC  GGC  GCG  TCC  ATG  GAG  ATC  CAC  CAG                         324
Ala  Tyr  Pro  Gly  Gly  Ala  Ser  Met  Glu  Ile  His  Gln
 85                      90                           95

GCA  CTC  ACC  CGC  TCC  CCC  GTC  ATC  GCC  AAC  CAC  CTC                         360
Ala  Leu  Thr  Arg  Ser  Pro  Val  Ile  Ala  Asn  His  Leu
                    100                      105

TTC  CGC  CAC  GAG  CAA  GGG  GAG  GCC  TTT  GCC  GCC  TCC                         396
Phe  Arg  His  Glu  Gln  Gly  Glu  Ala  Phe  Ala  Ala  Ser
          110                      115                 120

GGC  TAC  GCG  CGC  TCC  TCG  GGC  CGC  GTC  GGC  GTC  TGC                         432
Gly  Tyr  Ala  Arg  Ser  Ser  Gly  Arg  Val  Gly  Val  Cys
                    125                      130

ATC  GCC  ACC  TCC  GGC  CCC  GGC  GCC  ACC  AAC  CTA  GTC                         468
Ile  Ala  Thr  Ser  Gly  Pro  Gly  Ala  Thr  Asn  Leu  Val
          135                      140

TCC  GCG  CTC  GCC  GAC  GCG  CTG  CTC  GAT  TCC  GTC  CCC                         504
Ser  Ala  Leu  Ala  Asp  Ala  Leu  Leu  Asp  Ser  Val  Pro
145                      150                      155

ATG  GTC  GCC  ATC  ACG  GGA  CAG  GTG  CCG  CGA  CGC  ATG                         540
Met  Val  Ala  Ile  Thr  Gly  Gln  Val  Pro  Arg  Arg  Met
               160                      165

ATT  GGC  ACC  GAC  GCC  TTC  CAG  GAG  ACG  CCC  ATC  GTC                         576
Trp  Gly  Thr  Asp  Ala  Phe  Gln  Glu  Thr  Pro  Ile  Val
          170                      175                 180

GAG  GTC  ACC  CGC  TCC  ATC  ACC  AAG  CAC  AAC  TAC  CTG                         612
Glu  Val  Thr  Arg  Ser  Ile  Thr  Lys  His  Asn  Tyr  Leu
                    185                      190

GTC  CTC  GAC  GTC  GAC  GAC  ATC  CCC  CGC  GTC  GTG  CAG                         648
Val  Leu  Asp  Val  Asp  Asp  Ile  Pro  Arg  Val  Val  Gln
               195                      200

GAG  GCT  TTC  TTC  CTC  GCC  TCC  TCT  GGT  CGA  CCA  GGG                         684
Glu  Ala  Phe  Phe  Leu  Ala  Ser  Ser  Gly  Arg  Pro  Gly
205                      210                      215
```

| | | | | | | | | | | | |
|---|---|---|---|---|---|---|---|---|---|---|---|
| CCG | GTG | CTT | GTC | GAC | ATC | CCC | AAG | GAC | ATC | CAG | CAG | 720
| Pro | Val | Leu | Val | Asp | Ile | Pro | Lys | Asp | Ile | Gln | Gln |
| | | 220 | | | | | 225 | | | | |
| CAG | ATG | GCG | GTG | CCT | GTC | TGG | GAC | AAG | CCC | ATG | AGT | 756
| Gln | Met | Ala | Val | Pro | Val | Trp | Asp | Lys | Pro | Met | Ser |
| | 230 | | | | | 235 | | | | | 240 |
| CTG | CCT | GGG | TAC | ATT | GCG | CGC | CTT | CCC | AAG | CCC | CCT | 792
| Leu | Pro | Gly | Tyr | Ile | Ala | Arg | Leu | Pro | Lys | Pro | Pro |
| | | | | 245 | | | | | 250 | | |
| GCG | ACT | GAG | TTG | CTT | GAG | CAG | GTG | CTG | CGT | CTT | GTT | 828
| Ala | Thr | Glu | Leu | Leu | Glu | Gln | Val | Leu | Arg | Leu | Val |
| | | 255 | | | | | 260 | | | | |
| GGT | GAA | TCG | CGG | CGC | CCT | GTT | CTT | TAT | GTG | GGC | GGT | 864
| Gly | Glu | Ser | Arg | Arg | Pro | Val | Leu | Tyr | Val | Gly | Gly |
| 265 | | | | | 270 | | | | | 275 | |
| GCG | TGC | GCA | GCA | TCT | GGT | GAG | GAG | TTG | CGA | CGC | TTT | 900
| Ala | Cys | Ala | Ala | Ser | Gly | Glu | Glu | Leu | Arg | Arg | Phe |
| | | | 280 | | | | | 285 | | | |
| GTG | GAG | CTG | ACT | GGA | ATC | CCG | GTC | ACA | ACT | ACT | CTT | 936
| Val | Glu | Leu | Thr | Gly | Ile | Pro | Val | Thr | Thr | Thr | Leu |
| | 290 | | | | | 295 | | | | | 300 |
| ATG | GGC | CTC | GGC | AAC | TTC | CCC | AGC | GAC | GAC | CCA | CTG | 972
| Met | Gly | Leu | Gly | Asn | Phe | Pro | Ser | Asp | Asp | Pro | Leu |
| | | | | 305 | | | | | 310 | | |
| TCT | CTG | CGC | ATG | CTA | GGT | ATG | CAT | GGG | ACG | GTG | TAT | 1008
| Ser | Leu | Arg | Met | Leu | Gly | Met | His | Gly | Thr | Val | Tyr |
| | | 315 | | | | | 320 | | | | |
| GCA | AAT | TAT | GCA | GTG | GAT | AAG | GCC | GAT | CTG | TTG | CTT | 1044
| Ala | Asn | Tyr | Ala | Val | Asp | Lys | Ala | Asp | Leu | Leu | Leu |
| 325 | | | | | 330 | | | | | 335 | |
| GCA | CTT | GGT | GTG | CGG | TTT | GAT | GAT | CGT | GTG | ACA | GGG | 1080
| Ala | Leu | Gly | Val | Arg | Phe | Asp | Asp | Arg | Val | Thr | Gly |
| | | | | 340 | | | | | 345 | | |
| AAG | ATT | GAG | GCT | TTT | GCA | AGC | AGG | GCT | AAG | ATT | GTG | 1116
| Lys | Ile | Glu | Ala | Phe | Ala | Ser | Arg | Ala | Lys | Ile | Val |
| | | 350 | | | | | 355 | | | | 360 |
| CAC | GTT | GAT | ATT | GAT | CCG | GCT | GAG | ATT | GGC | AAG | AAC | 1152
| His | Val | Asp | Ile | Asp | Pro | Ala | Glu | Ile | Gly | Lys | Asn |
| | | | | 365 | | | | | 370 | | |
| AAG | CAG | CCA | CAT | GTG | TCC | ATC | TGT | GCA | GAT | GTT | AAG | 1188
| Lys | Gln | Pro | His | Val | Ser | Ile | Cys | Ala | Asp | Val | Lys |
| | | 375 | | | | | 380 | | | | |
| CTT | GCT | TTG | CAG | GGC | ATG | AAT | GCT | CTT | CTT | GAA | GGA | 1224
| Leu | Ala | Leu | Gln | Gly | Met | Asn | Ala | Leu | Leu | Glu | Gly |
| 385 | | | | | 390 | | | | | 395 | |
| AGC | ACA | TCA | AAG | AAG | AGC | TTT | GAC | TTT | GGC | TCA | TGG | 1260
| Ser | Thr | Ser | Lys | Lys | Ser | Phe | Asp | Phe | Gly | Ser | Trp |
| | | | 400 | | | | | 405 | | | |
| AAC | GAT | GAG | TTG | GAT | CAG | CAG | AAG | AGG | GAA | TTC | CCC | 1296
| Asn | Asp | Glu | Leu | Asp | Gln | Gln | Lys | Arg | Glu | Phe | Pro |
| | 410 | | | | | 415 | | | | | 420 |
| CTT | GGG | TAT | AAA | ACA | TCT | AAT | GAG | GAG | ATC | CAG | CCA | 1332
| Leu | Gly | Tyr | Lys | Thr | Ser | Asn | Glu | Glu | Ile | Gln | Pro |
| | | | | 425 | | | | | 430 | | |
| CAA | TAT | GCT | ATT | CAG | GTT | CTT | GAT | GAG | CTG | ACG | AAA | 1368
| Gln | Tyr | Ala | Ile | Gln | Val | Leu | Asp | Glu | Leu | Thr | Lys |
| | | 435 | | | | | 440 | | | | |
| GGC | GAG | GCC | ATC | ATC | GGC | ACA | GGT | GTT | GGG | CAG | CAC | 1404
| Gly | Glu | Ala | Ile | Ile | Gly | Thr | Gly | Val | Gly | Gln | His |
| 445 | | | | | 450 | | | | | 455 | |

| | | | | | | | | | | | |
|---|---|---|---|---|---|---|---|---|---|---|---|
| CAT | ATG | TGG | GCG | GCA | CAG | TAC | TAC | ACT | TAC | AAG | CGG | 1440
| Gln | Met | Trp | Ala | Ala | Gln | Tyr | Tyr | Thr | Tyr | Lys | Arg |
| | | 460 | | | | | | 465 | | | |
| CCA | AGG | CAG | TGG | TTG | TCT | TCA | GCT | GGT | CTT | GGG | GCT | 1476
| Pro | Arg | Gln | Trp | Leu | Ser | Ser | Ala | Gly | Leu | Gly | Ala |
| | 470 | | | | | 475 | | | | | 480 |
| ATG | GGA | TTT | GGT | TTG | CCG | GCT | GCT | GCT | GGT | GCT | TCT | 1512
| Met | Gly | Phe | Gly | Leu | Pro | Ala | Ala | Ala | Gly | Ala | Ser |
| | | | | 485 | | | | | 490 | | |
| GTG | GCC | AAC | CCA | GGT | GTC | ACT | GTT | GTT | GAC | ATC | GAT | 1548
| Val | Ala | Asn | Pro | Gly | Val | Thr | Val | Val | Asp | Ile | Asp |
| | | 495 | | | | | 500 | | | | |
| GGA | GAT | GGT | AGC | TTT | CTC | ATG | AAC | GTT | CAG | GAG | CTA | 1584
| Gly | Asp | Gly | Ser | Phe | Leu | Met | Asn | Val | Gln | Glu | Leu |
| 505 | | | | | 510 | | | | | 515 | |
| GCT | ATG | ATC | CGA | ATT | GAG | AAC | CTC | CCA | GTG | AAG | GTC | 1620
| Ala | Met | Ile | Arg | Ile | Glu | Asn | Leu | Pro | Val | Lys | Val |
| | | | 520 | | | | | 525 | | | |
| TTT | GTG | CTA | AAC | AAC | CAG | CAC | CTG | GGG | ATG | GTG | GTG | 1656
| Phe | Val | Leu | Asn | Asn | Gln | His | Leu | Gly | Met | Val | Val |
| | 530 | | | | | 535 | | | | | 540 |
| CAG | TGG | GAG | GAC | AGG | TTC | TAT | AAG | GCC | AAC | AGA | GCG | 1692
| Gln | Trp | Glu | Asp | Arg | Phe | Tyr | Lys | Ala | Asn | Arg | Ala |
| | | | | 545 | | | | | 550 | | |
| CAC | ACA | TAC | TTG | GGA | AAC | CCA | GAG | AAT | GAA | AGT | GAG | 1728
| His | Thr | Tyr | Leu | Gly | Asn | Pro | Glu | Asn | Glu | Ser | Glu |
| | | 555 | | | | | 560 | | | | |
| ATA | TAT | CCA | GAT | TTC | GTG | ACG | ATC | GCC | AAA | GGG | TTC | 1764
| Ile | Tyr | Pro | Asp | Phe | Val | Thr | Ile | Ala | Lys | Gly | Phe |
| 565 | | | | | 570 | | | | | 575 | |
| AAC | ATT | CCA | GCG | GTC | CGT | GTG | ACA | AAG | AAG | AAC | GAA | 1800
| Asn | Ile | Pro | Ala | Val | Arg | Val | Thr | Lys | Lys | Asn | Glu |
| | | | 580 | | | | | 585 | | | |
| GTC | CGC | GCA | GCG | ATA | AAG | AAG | ATG | CTC | GAG | ACT | CCA | 1836
| Val | Arg | Ala | Ala | Ile | Lys | Lys | Met | Leu | Glu | Thr | Pro |
| | 590 | | | | | 595 | | | | | 600 |
| GGG | CCG | TAC | CTC | TTG | GAT | ATA | ATC | GTC | CCA | CAC | CAG | 1872
| Gly | Pro | Tyr | Leu | Leu | Asp | Ile | Ile | Val | Pro | His | Gln |
| | | | | 605 | | | | | 610 | | |
| GAG | CAT | GTG | TTG | CCT | ATG | ATC | CCT | AGT | GGT | GGG | GCT | 1908
| Glu | His | Val | Leu | Pro | Met | Ile | Pro | Ser | Gly | Gly | Ala |
| | | 615 | | | | | 620 | | | | |
| TTC | AAG | GAT | ATG | ATC | CTG | GAT | GGT | GAT | GGC | AGG | ACT | 1944
| Phe | Lys | Asp | Met | Ile | Leu | Asp | Gly | Asp | Gly | Arg | Thr |
| 625 | | | | | 630 | | | | | 635 | |
| GTG | TAC | | | | | | | | | | | 1950
| Val | Tyr | | | | | | | | | | |
| | 638 | | | | | | | | | | |
| TGATCTAAAA | TCCAGCAAG | | | | | | | | | | | 1969